(12) United States Patent
Truckai et al.

(10) Patent No.: US 10,695,117 B2
(45) Date of Patent: Jun. 30, 2020

(54) BONE TREATMENT SYSTEMS AND METHODS

(71) Applicant: DFINE, Inc., South Jordan, UT (US)

(72) Inventors: Csaba Truckai, Saratoga, CA (US); Andrew Kohm, San Mateo, CA (US); John H. Shadduck, Tiburon, CA (US)

(73) Assignee: DFine, Inc., South Jordan, UT (US)

( * ) Notice: Subject to any disclaimer, the term of this patent is extended or adjusted under 35 U.S.C. 154(b) by 1177 days.

(21) Appl. No.: 14/887,030

(22) Filed: Oct. 19, 2015

(65) Prior Publication Data

US 2016/0106489 A1    Apr. 21, 2016

Related U.S. Application Data

(62) Division of application No. 12/728,127, filed on Mar. 19, 2010, now Pat. No. 9,161,798.

(60) Provisional application No. 61/210,496, filed on Mar. 19, 2009.

(51) Int. Cl.
  *A61B 17/88* (2006.01)
  *A61B 90/98* (2016.01)
  *A61B 17/00* (2006.01)

(52) U.S. Cl.
  CPC .......... *A61B 17/8836* (2013.01); *A61B 90/98* (2016.02); *A61B 17/8822* (2013.01); *A61B 2017/00084* (2013.01)

(58) Field of Classification Search
  CPC .................. A61B 17/8833; A61B 17/8836
  USPC ...................................... 606/92–94
  See application file for complete search history.

(56) References Cited

U.S. PATENT DOCUMENTS

| | | |
|---|---|---|
| 3,349,840 A | 10/1967 | Tope et al. |
| 4,377,168 A | 3/1983 | Rzasa et al. |
| 5,130,950 A | 7/1992 | Orban et al. |
| 5,145,250 A | 9/1992 | Planck et al. |
| 5,542,928 A | 8/1996 | Evans et al. |
| 5,788,711 A | 8/1998 | Lehner et al. |
| 5,954,716 A | 9/1999 | Sharkey et al. |
| 6,075,067 A | 6/2000 | Lidgren |
| 6,086,594 A | 7/2000 | Brown |
| 6,122,549 A | 9/2000 | Sharkey et al. |

(Continued)

FOREIGN PATENT DOCUMENTS

| | | |
|---|---|---|
| EP | 2 319 439 | 5/2011 |
| WO | WO 02/058592 | 8/2002 |

(Continued)

OTHER PUBLICATIONS

International Search Report, dated Sep. 24, 2009, PCT/US2008/061911, 15 pgs.

(Continued)

*Primary Examiner* — Si Ming Ku
(74) *Attorney, Agent, or Firm* — Stoel Rives LLP

(57) ABSTRACT

Systems and methods for treating vertebral compression fractures are provided. A kit can include at least one body containing a bone cement precursor to be mixed with at least one other bone cement precursor to form a bone cement. The body or a package containing the body can include at least one sensor. In some embodiments the sensor can be a temperature sensor. In some methods, data from the sensor can be used to determine certain parameters related to a treatment interval involving the bone cement.

15 Claims, 27 Drawing Sheets

(56) References Cited

U.S. PATENT DOCUMENTS

| | | |
|---|---|---|
| 6,174,319 B1 | 1/2001 | Desnos |
| 6,231,615 B1 | 5/2001 | Preissman |
| 6,235,043 B1 | 5/2001 | Reiley et al. |
| 6,241,734 B1 | 6/2001 | Scribner |
| 6,264,659 B1 | 7/2001 | Ross et al. |
| 6,280,456 B1 | 8/2001 | Scribner et al. |
| 6,309,420 B1 | 10/2001 | Preissman |
| 6,436,143 B1 | 8/2002 | Ross et al. |
| 6,458,127 B1 | 10/2002 | Truckai et al. |
| 6,613,018 B2 | 9/2003 | Bagga et al. |
| 6,632,235 B2 | 10/2003 | Weikel et al. |
| 6,726,691 B2 | 4/2004 | Osorio et al. |
| 6,736,537 B2 | 5/2004 | Coffeen et al. |
| 6,753,358 B2 | 6/2004 | Fischer et al. |
| 6,783,515 B1 | 8/2004 | Miller |
| 6,814,736 B2 | 11/2004 | Reiley et al. |
| 6,832,988 B2 | 12/2004 | Sproul |
| 6,929,640 B1 | 8/2005 | Underwood |
| 6,958,061 B2 | 10/2005 | Truckai et al. |
| 6,964,667 B2 | 11/2005 | Shaolian et al. |
| 6,979,341 B2 | 12/2005 | Scribner et al. |
| 6,979,352 B2 | 12/2005 | Reynolds |
| 7,008,433 B2 | 3/2006 | Voellmicke et al. |
| 7,108,696 B2 | 9/2006 | Daniel et al. |
| 7,112,201 B2 | 9/2006 | Truckai et al. |
| 7,153,306 B2 | 12/2006 | Ralph et al. |
| 7,153,307 B2 | 12/2006 | Scribner et al. |
| 7,166,121 B2 | 1/2007 | Reiley et al. |
| 7,241,303 B2 | 7/2007 | Reiss et al. |
| 7,261,720 B2 | 8/2007 | Stevens et al. |
| 7,559,932 B2 | 7/2009 | Truckai et al. |
| 7,678,116 B2 | 3/2010 | Truckai et al. |
| 7,708,733 B2 | 5/2010 | Sanders et al. |
| 7,968,616 B2 | 6/2011 | Meyer et al. |
| 8,215,835 B2 * | 7/2012 | Hyde .................. A61J 1/165 374/208 |
| 8,609,746 B2 | 12/2013 | Nakamura et al. |
| 2002/0026195 A1 | 2/2002 | Layne et al. |
| 2002/0147497 A1 | 10/2002 | Belef et al. |
| 2003/0130738 A1 | 7/2003 | Hovda et al. |
| 2003/0220648 A1 | 11/2003 | Osorio et al. |
| 2003/0233096 A1 | 12/2003 | Osorio et al. |
| 2004/0024410 A1 | 2/2004 | Olson |
| 2004/0083002 A1 | 4/2004 | Belef et al. |
| 2004/0110285 A1 | 6/2004 | Lendlein |
| 2004/0172132 A1 | 9/2004 | Ginn |
| 2005/0113843 A1 | 5/2005 | Arramon |
| 2005/0222681 A1 | 10/2005 | Richley et al. |
| 2005/0245938 A1 | 11/2005 | Kochan |
| 2005/0251149 A1 | 11/2005 | Wenz |
| 2006/0052743 A1 | 3/2006 | Reynolds |
| 2006/0052794 A1 | 3/2006 | McGill et al. |
| 2006/0074433 A1 | 4/2006 | McGill et al. |
| 2006/0079905 A1 | 4/2006 | Beyar et al. |
| 2006/0106459 A1 | 5/2006 | Truckai et al. |
| 2006/0122621 A1 | 6/2006 | Truckai et al. |
| 2006/0150862 A1 | 7/2006 | Zhao et al. |
| 2007/0027230 A1 | 2/2007 | Beyar et al. |
| 2007/0112299 A1 | 5/2007 | Smit et al. |
| 2007/0154874 A1 | 7/2007 | Sherman et al. |
| 2007/0162043 A1 | 7/2007 | Truckai et al. |
| 2007/0185231 A1 | 8/2007 | Liu et al. |
| 2007/0191858 A1 | 8/2007 | Truckai et al. |
| 2008/0065083 A1 | 3/2008 | Truckai et al. |
| 2008/0103505 A1 | 5/2008 | Fransen |
| 2008/0195112 A1 | 8/2008 | Liu et al. |
| 2009/0024161 A1 | 1/2009 | Bonutti et al. |
| 2009/0112365 A1 | 4/2009 | Orr et al. |
| 2009/0131945 A1 | 5/2009 | Liu et al. |
| 2009/0247664 A1 | 10/2009 | Truckai et al. |
| 2009/0281549 A1 * | 11/2009 | Dixon ................ B01F 7/00266 606/94 |
| 2010/0168271 A1 * | 7/2010 | Beyar .................... A61L 24/046 523/116 |

FOREIGN PATENT DOCUMENTS

| | | |
|---|---|---|
| WO | WO 02/064062 | 8/2002 |
| WO | WO 02/087416 | 11/2002 |
| WO | WO 04/075954 | 9/2004 |
| WO | WO 06/031490 | 3/2006 |
| WO | WO 06/062916 | 6/2006 |
| WO | WO 06/062939 | 6/2006 |
| WO | WO 06/090379 | 8/2006 |
| WO | WO 06/130491 | 12/2006 |
| WO | WO 07/028120 | 3/2007 |
| WO | WO 07/148336 | 12/2007 |
| WO | WO 08/124533 | 10/2008 |

OTHER PUBLICATIONS

International Search Report, dated Apr. 16, 2007, PCT/US2006/034409.

* cited by examiner

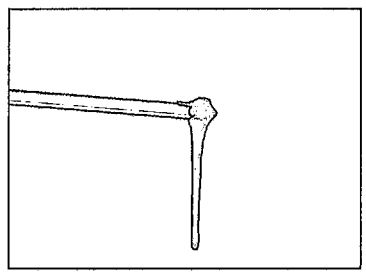 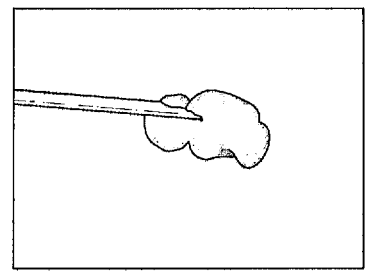
FIG. 8C  FIG. 8D

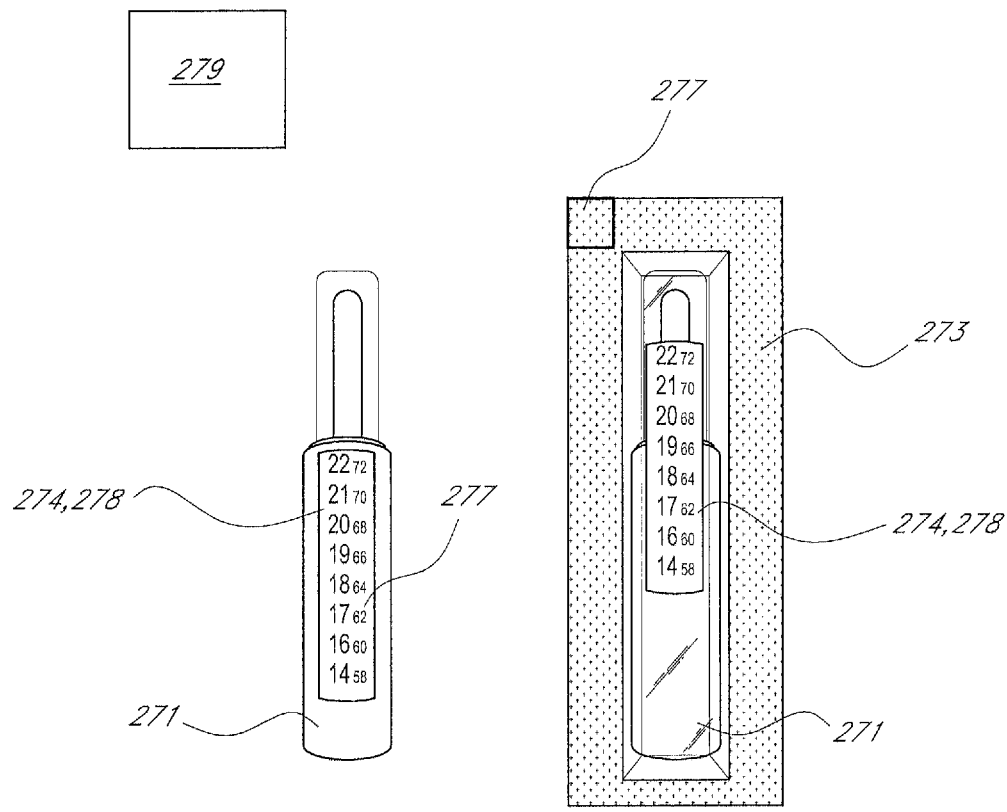
FIG. 27  FIG. 28

BONE TREATMENT SYSTEMS AND METHODS

CROSS-REFERENCE TO RELATED APPLICATIONS

This application is a divisional of U.S. patent application Ser. No. 12/728,127, filed Mar. 19, 2010, which claims the benefit of priority under 35 U.S.C. § 119(e) of U.S. Provisional Application No. 61/210,496 filed Mar. 19, 2009. This application is also related to U.S. patent application Ser. No. 12/024,969, filed on Feb. 1, 2008; Ser. No. 12/395,532, filed on Feb. 27, 2009; and Ser. No. 12/512,505, filed on Jul. 30, 2009. The entire contents of all of the above applications are hereby incorporated by reference and should be considered a part of this specification.

BACKGROUND OF THE INVENTION

Field of the Invention

Embodiments of the present disclosure relate to bone cements and cement injection systems, and in some embodiments provide systems and methods for on-demand control of bone cement viscosity for treating vertebral compression fractures and for preventing cement extravasation.

Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts, and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of polymethyl methacrylate (PMMA) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA or more is used on each side of the vertebra. Since the PMMA needs to be forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique, as the physician generally terminates PMMA injection when leakage is observed. The cement is injected using syringes to allow the physician manual control of injection pressure.

Balloon kyphoplasty is a modification of percutaneous vertebroplasty. Balloon kyphoplasty involves a preliminary step comprising the percutaneous placement of an inflatable balloon tamp in the vertebral body. Inflation of the balloon creates a cavity in the bone prior to cement injection. In balloon kyphoplasty, the PMMA cement can be injected at a lower pressure into the collapsed vertebra since a cavity exists, as compared to conventional vertebroplasty. More recently, other forms of kyphoplasty have been developed in which various tools are used to create a pathway or cavity into which the bone cement is then injected.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture, and the visibility and degree of involvement of the pedicles.

Leakage of PMMA during vertebroplasty can result in very serious complications including compression of adjacent structures that necessitate emergency decompressive surgery. See Groen, R. et al., "Anatomical and Pathological Considerations in Percutaneous Vertebroplasty and Kyphoplasty: A Reappraisal of the Vertebral Venous System," Spine Vol. 29, No. 13, pp 1465-1471, 2004. Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al., "The Analysis of Polymethylmethacrylate Leakage after Vertebroplasty for Vertebral Body Compression Fractures," J. of Korean Neurosurg. Soc., Vol. 35, No. 5 (May 2004), pp 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol., 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al., "Asymptomatic Diffuse Pulmonary Embolism Caused by Acrylic Cement: An Unusual Complication of Percutaneous Vertebroplasty," Ann. Rheum. Dis., 62:85-86, 2003. The vapors from PMMA preparation and injection also are cause for concern. See Kirby, B, et al., "Acute Bronchospasm Due to Exposure to Polymethylmethacrylate Vapors During Percutaneous Vertebroplasty," Am. J. Roentgenol., 180:543-544, 2003.

SUMMARY OF THE INVENTION

There is a general need to provide bone cements and methods for use in treatment of vertebral compression fractures that provide a greater degree of control over introduction of cement and that provide better outcomes. The present disclosure meets this need and provides several other advantages in a novel and nonobvious manner.

In some embodiments, a system for providing a bone cement for injection into a patient, can comprise a bone cement kit and a data transmitter. The bone cement kit can include one or more packages of bone cement precursors, wherein the bone cement precursors are configured to combine to form a bone cement. The data transmitter can be carried by at least one of the one or more packages and can be configured to communicate output data. In some embodiments, the system can further include a data receiver. The data receiver can be configured to receive the output data from the data transmitter and for providing a signal to one or both of an electronic controller and system operator.

In some embodiments, the signal indicates at least one of a cement temperature and a post-mixing start time for injecting the cement. In some embodiments, the output data can comprise at least one ID parameter selected from the group of monomer or polymer type, volume of monomer or polymer, and manufacturing lot of the monomer of polymer. In some embodiments, the output data can comprises at least one of a temperature of a monomer or polymer, and a temperature log of a monomer or polymer.

Certain embodiments can comprise a system for providing a bone cement for injection into a patient. The system can include a bone cement kit and a data receiver. The bone cement kit of some embodiments can comprise one or more packages of bone cement components, wherein the bone cement components are configured to combine to form a bone cement and include a liquid monomer component and a powder component. The data receiver can be configured to receive output data concerning the bone cement components from a data transmitter and for providing a signal to one or both of an electronic controller and system operator.

In some embodiments, the signal can indicate at least one of a cement temperature and a post-mixing start time for injecting the cement. In some embodiments, the system can further include the data transmitter which can be connected to one of the one or more packages.

A system for providing a bone cement for injection into a patient according to some embodiments can comprise a bone cement kit and at least one temperature sensor. The bone cement kit can comprise one or more packages of bone cement components, wherein the bone cement components are configured to combine to form a bone cement and include a liquid monomer component and a powder component. The at least one temperature sensor can be affixed to at least one package of the bone cement components. In some embodiments, the sensor can be configured to indicate the temperature of said bone cement component.

In some embodiments, the one or more packages can comprise at least one of a vial, ampule, tube, syringe, shipping carton, box, bag, sterile pouch, sterile sac and blister pack. In some embodiments, the temperature sensor can comprise a temperature strip, and/or a thermochromic ink. In some embodiments, the temperature sensor can be affixed to the package of liquid monomer component.

Embodiments of a method for providing operational information concerning a bone cement, can include various steps. A method can include providing a bone cement kit. The bone cement kit can include one or more packages of bone cement precursors, wherein the bone cement precursors combine to form a bone cement. In some embodiments, at least one of the one or more packages can have a radio frequency tag affixed thereto. A method can include receiving a signal from a radio frequency tag indicating data of one or more bone cement precursors. A method can include mixing bone cement precursors to form bone cement. A method can further include determining an operational step for the use of the bone cement based on the data.

In some embodiments, receiving the signal from the radio frequency tag can be in response to an interrogation signal communicated from a controller to the one or more packages. In some embodiments, the data can be at least one of temperature and temperature history. In some embodiments, the operational step can be wait time post-mixing.

A method for providing operational information concerning a bone cement according to some embodiments can comprise providing a bone cement kit comprising at least two packages of bone cement precursors and mixing the bone cement precursors to provide a bone cement. In some embodiments, the bone cement kit can further include at least one temperature sensor affixed to one of the packages of bone cement precursors. The method can also include the step of determining a bone cement injection start time based on temperature from the at least one temperature sensor.

In some embodiments, the determining step can be derived from a chart and/or provided by an algorithm and computer controller.

According to some embodiments, a method is provide for determining a working condition of a curable bone cement. The method can comprise one or more of the following steps: determining a pre-mix temperature of at least one of first and second bone cement precursors; determining an ambient temperature; mixing the first and second bone cement precursors to form a bone cement; and determining a bone cement injection start time based at least in part on an algorithm relating to said pre-mix and ambient temperatures.

In some embodiment the method can further include one or more of the following steps: actuating a controller and energy source to apply energy through an emitter to thereby apply heat to the bone cement post-mixing; actuating the controller to modulate applied energy based on the pre-mix and ambient temperatures and/or the calculated injection start time; and actuating the controller to modulate hydraulic pressure based on the pre-mix and ambient temperatures and/or the calculated injection start time.

In some embodiments, the determining steps can be accomplished at least by a temperature sensor affixed to containers and/or packaging of the first and second bone cement precursors. In some embodiments, determining the pre-mix temperature can comprise determining a pre-mix temperature history of at least one of first and second bone cement precursors.

BRIEF DESCRIPTION OF THE DRAWINGS

In order to better understand the embodiments of the present disclosure and to see how it may be carried out in practice, some preferred embodiments are next described, by way of non-limiting examples only, with reference to the accompanying drawings, in which like reference characters denote corresponding features consistently throughout similar embodiments in the attached drawings.

FIGS. 8C and 8D are images of PMMA bone cement exiting an injector. FIG. 8C is PMMA bone cement exiting the injector without applied energy and FIG. 8D is the same PMMA bone cement exiting an injector as modified by applied energy according to one embodiment of energy-delivery algorithm.

FIG. 27 shows a temperature sensor affixed to a vial containing a bone cement precursor.

FIG. 28 illustrates a temperature sensor affixed to packaging of a bone cement precursor.

DETAILED DESCRIPTION OF THE PREFERRED EMBODIMENTS

Figure 1:
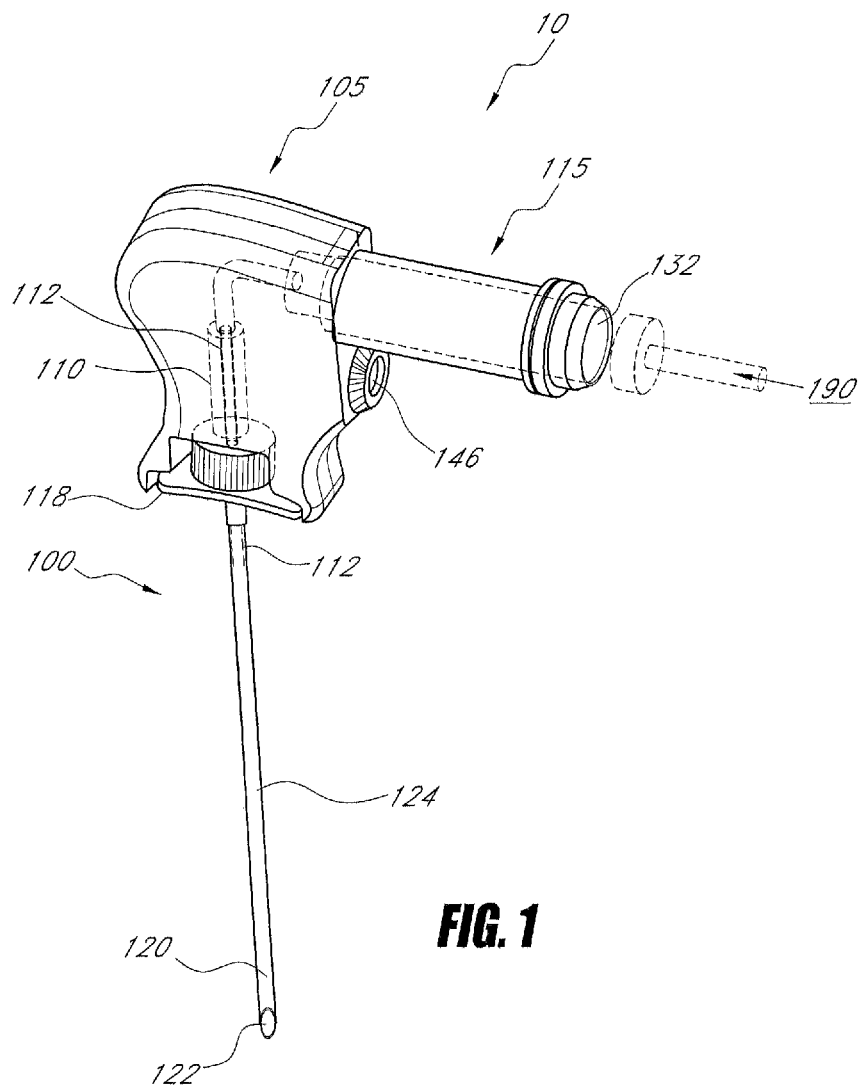
FIG. 1 is a schematic, perspective view of a bone cement injection system in accordance with one embodiment.

For purposes of understanding the principles of the embodiments of the present disclosure, reference will now be made to the embodiments illustrated in the drawings and accompanying text. As background, a vertebroplasty procedure using embodiments of the present disclosure may introduce the injector of FIGS. 1-2 through a pedicle of a vertebra, or in a parapedicular approach, for accessing the osteoporotic cancellous bone. The initial aspects of the procedure can be similar to percutaneous vertebroplasty wherein the patient is placed in a prone position on an operating table. The patient is typically under conscious sedation, although general anesthesia is an alternative. The physician injects a local anesthetic (e.g., about 1% Lidocaine) into the region overlying the targeted pedicle or pedicles, as well as the periosteum of the pedicle(s). Thereafter, the physician may use a scalpel to make an approximately 1 to 5 mm skin incision over each targeted pedicle. Thereafter, a bone cement injector can be advanced through the pedicle into the anterior region of the vertebral body, which typically is the region of greatest compression and fracture. The physician confirms the introducer path posterior to the pedicle, through the pedicle and within the vertebral body, by anteroposterior and lateral X-Ray projection fluoroscopic views or by other methods. The introduction of infill material as described below can be imaged several times, or continuously, during the treatment depending on the imaging method.

The terms "bone cement," "bone fill," "bone fill material," "infill material," and "infill composition" include their ordinary meaning as known to those skilled in the art and may include any material for infilling a bone that includes an in-situ hardenable or settable cement and compositions that can be infused with such a hardenable cement. The fill material also can include other fillers, such as filaments, microspheres, powders, granular elements, flakes, chips, tubules and the like, autograft or allograft materials, as well as other chemicals, pharmacological agents, or other bioactive agents.

The term "flowable material" includes its ordinary meaning as known to those skilled in the art and may include a material continuum that is unable to withstand any static shear stress and responds with a substantially irrecoverable flow (e.g., a fluid), unlike an elastic material or elastomer that responds to shear stress with a recoverable deformation. Flowable materials may include fill material or composites that may include a first, fluid component alone or in combination with a second, elastic, or inelastic material component that responds to stress with a flow, no matter the proportions of the first and second component. It may be understood that the above shear test does not apply to the second component alone.

The term "vertebroplasty" includes its ordinary meaning as known to those skilled in the art and may include any procedure where fill material is delivered into the interior of a vertebra.

The term "osteoplasty" includes its ordinary meaning as known to those skilled in the art and may include any procedure where a fill material is delivered into the interior of a bone.

Figure 2:
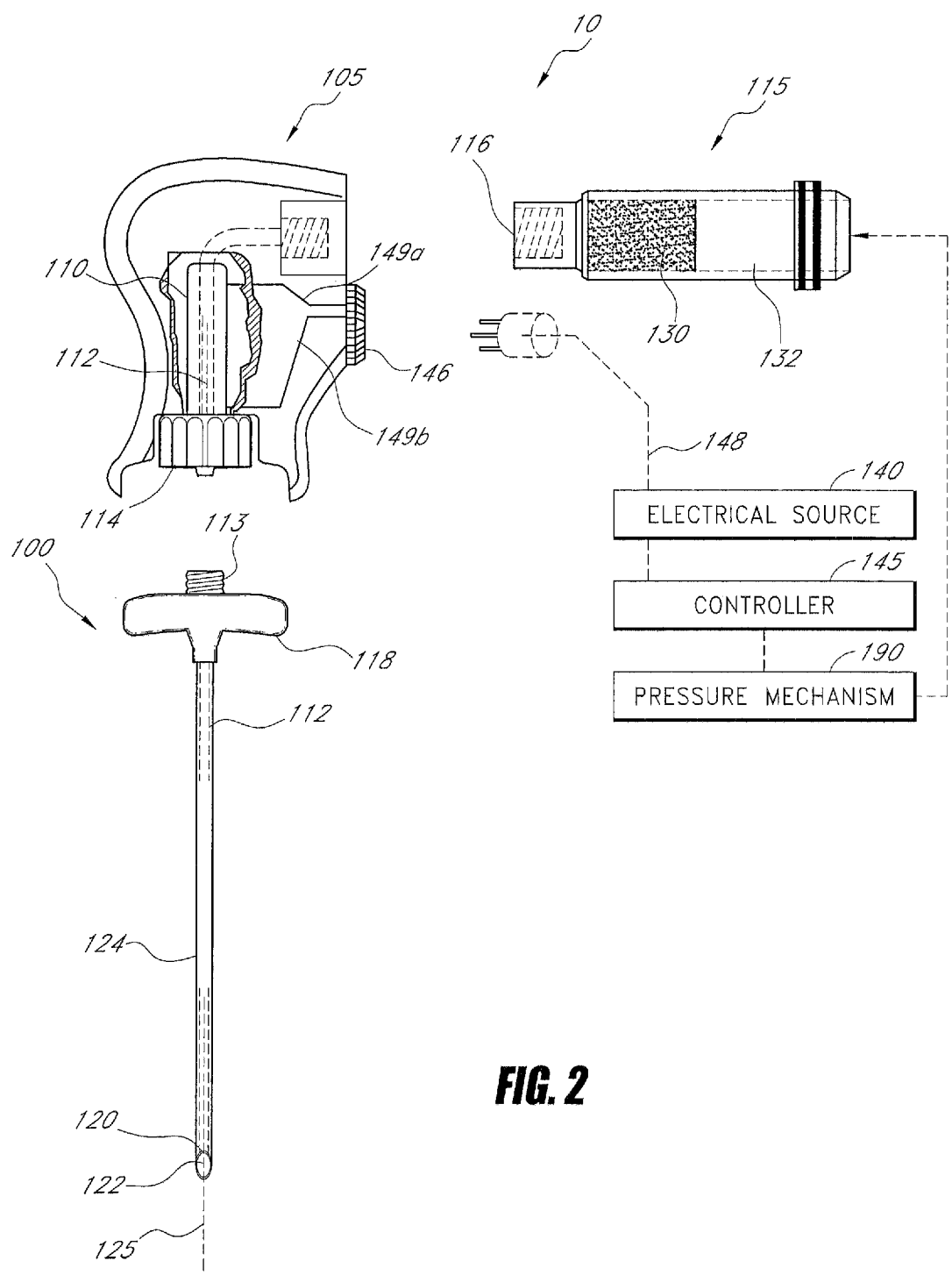
FIG. 2 is a schematic, exploded side view of the system of FIG. 1 illustrating some of the bone cement injection components de-mated from one another.

In FIG. 1, an embodiment of a system 10 is shown that includes a first component or bone cement injector 100 which may extend into cancellous bone of a vertebra, and a second component or cement activation component 105 which includes an emitter 110 for applying energy to bone cement. The first and second components 100 and 105 may include a flow passageway or channel 112 extending therethrough for delivering flowable bone cement into a bone. The bone cement injector component 100 and the cement activation component 105 can be integrated into a unitary device or can be de-mateable, as shown in FIG. 2, by a mechanism such as a threaded portion 113 and a rotatable screw-on fitting 114. Other configurations are also possible. As can be seen in FIGS. 1 and 2, a source of bone cement in the form of a syringe-type body 115 can also couple to the system, for example, by way of a threaded fitting 116.

Referring to FIG. 2, the bone cement injector 100 may include a proximal end 118 and a distal end 120 with at least one flow outlet 122 therein to direct a flow of cement into a bone. The extension portion 124 of the injector 100 can be made of any suitable metal or plastic sleeve with flow channel 112 extending therethrough to the flow outlet 122. The flow outlet 122 may be present as a side port to direct cement flow transverse relative to the axis 125 of extension portion 124 or, alternatively, can be positioned at the distal termination of extension portion 124 in order to direct cement flows distally. In another embodiment (not shown) the extension portion 124 can include first and second concentric sleeves that can be positioned so as to be rotated relative to one another to align or misalign respective first and second flow outlets to allow selectively directed cement flows to be more or less axial relative to axis 125 of extension portion 124.

Now turning to the cut-away view of FIG. 2, it can be seen that second component 105 includes a handle portion that carries an emitter 110 for applying thermal energy to a cement flow within the flow channel 112 that extends through the emitter 110. As will be described further below, the emitter 110 may apply thermal energy to bone cement 130 delivered from chamber 132 of source 115 to flow through the emitter 110 to therein cause the viscosity of the cement to increase to a selected, higher viscosity value as the cement exits the injector flow outlet 122 into bone. The controlled application of energy to bone cement 130 may enable the physician to select a setting rate for the cement to reach a selected polymerization endpoint as the cement is being introduced into the vertebra, for example, allowing a high viscosity that will prevent unwanted cement extravasation.

Figure 3:
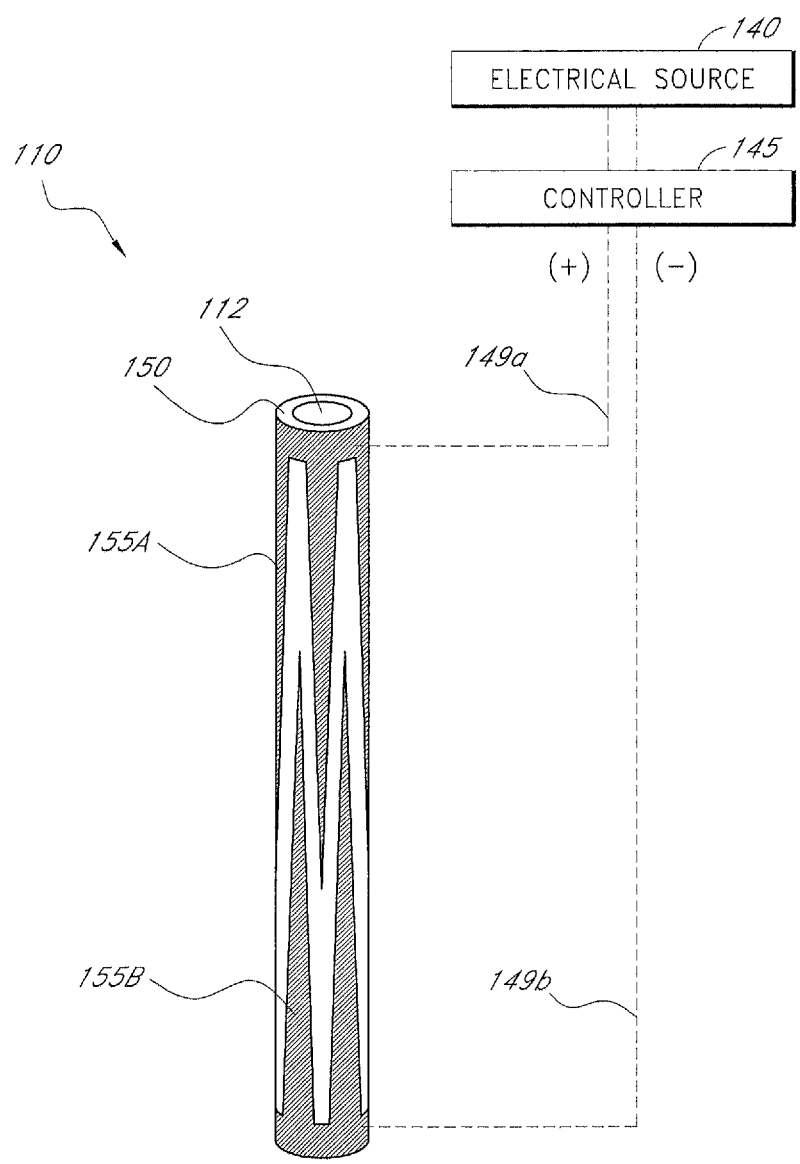
FIG. 3 is a schematic illustration of one embodiment of a thermal emitter component of the system of FIGS. 1 and 2.

Referring to FIGS. 2 and 3, in one embodiment, the thermal energy emitter 110 may be coupled to an electrical source 140 and controller 145 by an electrical connector 146 and a cable 148. In FIG. 2, it can be seen that electrical leads 149a and 149b may be coupled with connector 146 and extend to the emitter 110. As can be seen in FIG. 3, one embodiment of thermal energy emitter 110 has a wall portion 150 that includes a polymeric positive temperature coefficient of resistance (PTCR) material with spaced apart interlaced surface electrodes 155A and 155B as described in Provisional Application No. 60/907,469 filed Apr. 3, 2007 titled Bone Treatment Systems and Methods. In this embodiment, the thermal emitter 110 and wall 150 thereof may resistively heat to thereby cause controlled thermal effects in bone cement 130 flowing therethrough. It may be appreciated that FIG. 3 is a schematic representation of one embodiment of thermal energy emitter 110 which can have any elongated or truncated shape or geometry, tapered or non-tapered form, or include the wall of a collapsible thin-wall element. Further, the positive (+) and negative (−) polarity electrodes 155A and 155B can have any spaced apart arrangement, for example radially spaced apart, helically spaced apart, axially spaced apart or any combination thereof. This resistively heated PTCR material of the emitter 110 may further generate a signal that indicates flow rate as described in Provisional Application No. 60/907,469 which in turn can be utilized by controller 145 to modulate energy applied to the bone cement therein, and/or modulate the flow rate of cement 130, which can be driven by a motor or stored energy mechanism. In another embodiment, the emitter can be any non-PTCR resistive heater such as a resistive coil heater.

In other embodiments, the thermal energy emitter 110 can include a PTCR constant temperature heater as described above or may include one or more of a resistive heater, a fiber optic emitter, a light channel, an ultrasound transducer, an electrode and an antenna. Accordingly, in any such embodiment, the energy source 140 can include at least one of a voltage source, a radiofrequency source, an electromagnetic energy source, a non-coherent light source, a laser source, an LED source, a microwave source, a magnetic source and an ultrasound source that is operatively coupled to the emitter 110.

Referring FIG. 2, it can be understood that a pressure mechanism 190 is coupleable to a bone cement source or a syringe 115 for driving the bone cement 130 through the system 10. The pressure mechanism 190 can include any suitable manual drive system or an automated drive system such as any pump, screw drive, pneumatic drive, hydraulic drive, cable drive or the like. Such automated drive systems may be coupled to controller 145 to modulate the flow rate of cement through the system.

Figure 4:
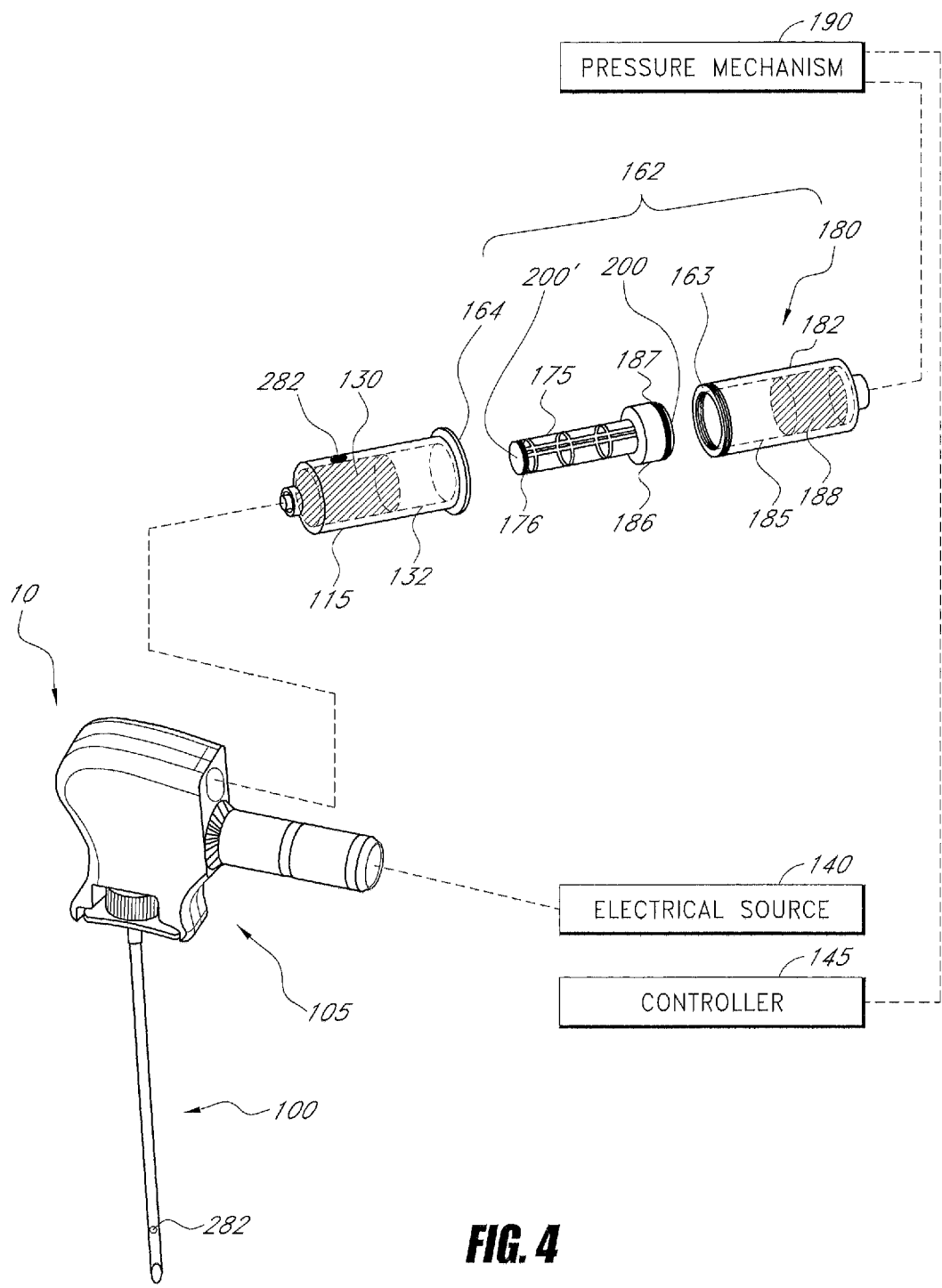
FIG. 4 is a schematic, exploded perspective view components of the system of FIGS. 1-2 in combination with an embodiment of a force application and amplification system, a pressurization mechanism and in communication with an energy source and a controller.
Figure 5:
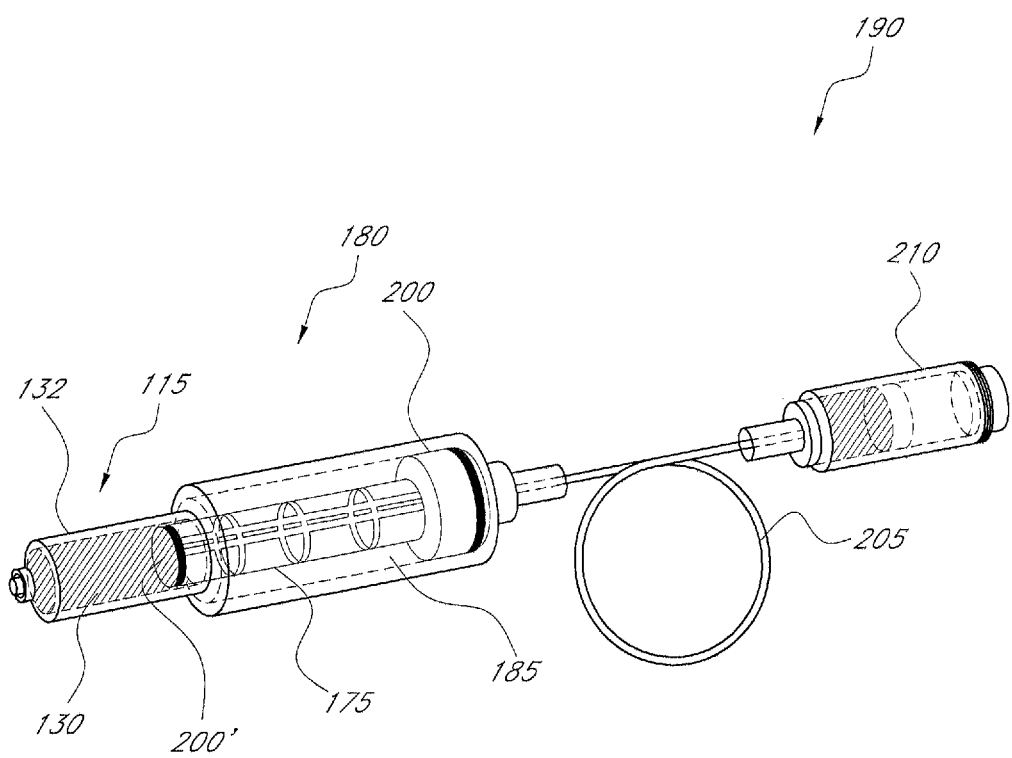
FIG. 5 is an enlarged, assembly view of an embodiment of a force application and amplification system and a pressurization mechanism of the system of FIG. 4.
Figure 6:
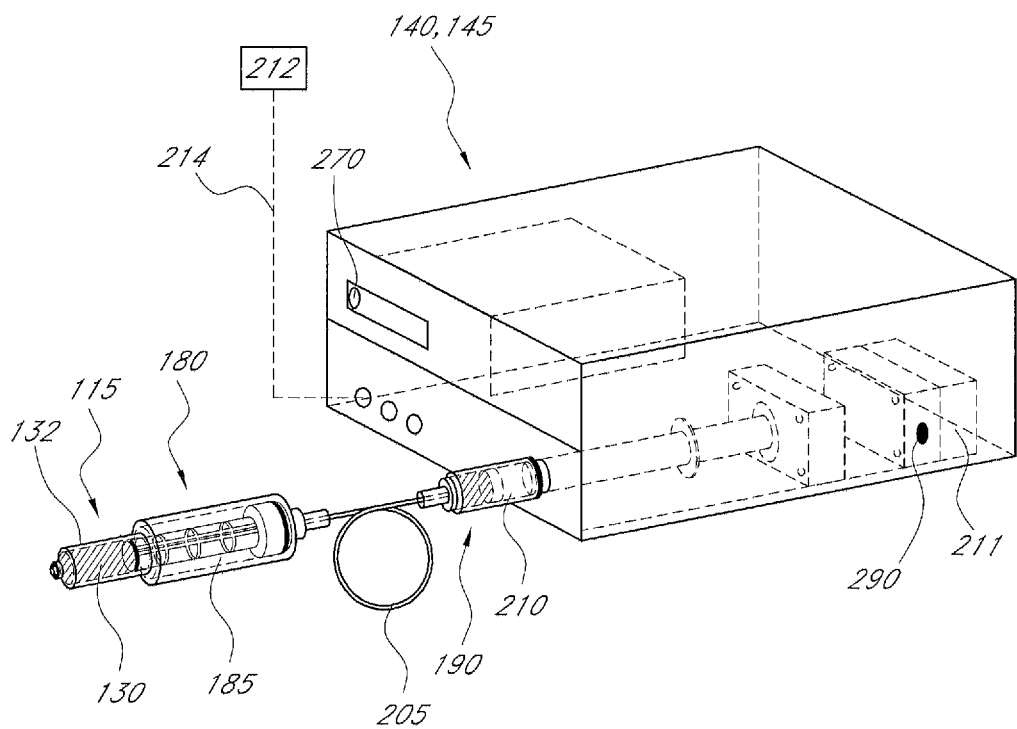
FIG. 6 is a perspective view of some of the components of the system of FIGS. 1-5 with a perspective view of an embodiment of an energy source and controller.
Figure 6:
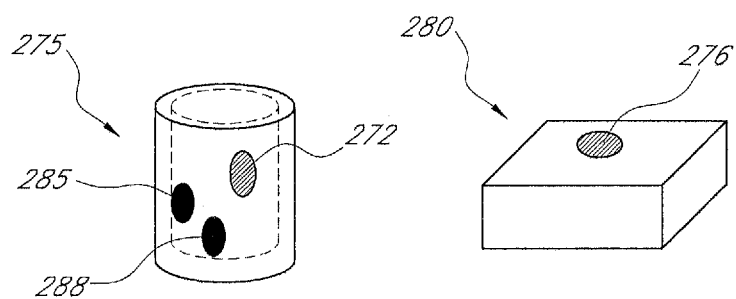

In one embodiment, shown in FIGS. 4-6, the system 10 may further include a hydraulic system 162 with a fitting 163 that may detachably couple to fitting 164 of the bone cement source 115. In this embodiment, the bone cement source 115 may include a syringe body with cement-carrying bore or chamber 132 that carries a pre-polymerized, partially polymerized or recently-mixed bone cement 130 therein. The hydraulic system 162 may further include a rigid plunger or actuator member 175 with o-ring or rubber head 176 that may move in chamber 132 so as to push the cement 130 through the syringe chamber 132 and the flow channel 112 in the system 100.

Still referring to FIGS. 4-6, a force application and amplification component 180 of the hydraulic system 162 may be reversibly couple to the bone cement source 115, where the force application and amplification component 180 includes a body 182 with pressurizable bore or chamber 185 therein that slidably receives the proximal end 186 of an actuator member 175. The proximal end 186 of actuator member 175 may include an o-ring or gasket 187 so that the bore 185 can be pressurized with flow media 188 by the pressure source 190 in order to drive the actuator member 175 distally to thereby displace bone cement 130 from the chamber 132 in the cement source or syringe 115. In one embodiment, illustrated in FIG. 5, the surface area of an interface 200 between the actuator member 175 and pressurized flow media 188 may be larger than the surface area of an interface 200' between the actuator member 175 and the bone cement 130 so as to thereby provide pressure amplification between the pressurizable chamber 185 and chamber 132 of the cement source or syringe. In one embodiment, as indicated in FIGS. 4 and 5, the surface area of interface 200 may be at least about 150% of the surface area of interface 200', at least about 200% of the surface area of interface 200', at least about 250% of the surface area of interface 200' and at least about 300% of the surface area of interface 200'.

Referring to FIGS. 4 and 5, in one embodiment, a force application and amplification component 188 may be employed in the following manner. In a first operation, a bone fill material injector with a displaceable, non-fluid actuator component intermediate a first fluid chamber and a second cement or fill-carrying chamber may be provided. In a second operation, a flow of media may be provided into the first fluid chamber at a first pressure to thereby displace the actuator component to impinge on and eject bone cement or fill at a higher second pressure from the second chamber into a vertebra. In a non-limiting example, a second pressure may be provided in the cement-carrying chamber 132 that is greater than the first pressure in the pressurizable chamber 185.

In one embodiment, the second pressure may be at least about 50% higher than the first pressure in the pressurizable chamber 185. In another embodiment, the second pressure may be at least about 75% higher than the first pressure in the pressurizable chamber 185. In another embodiment, the second pressure may be at least about 100% higher than the first pressure in the pressurizable chamber 185. In another embodiment, the second pressure may be at least about 200% higher than the first pressure in the pressurizable chamber 185. In another embodiment, the second pressure may be at least about 300% higher than the first pressure in the pressurizable chamber 185.

Referring to FIGS. 5 and 6, one embodiment of pressurizing mechanism for providing pressure to the force application and amplification component 180 may include a pneumatic or hydraulic line 205 that extends to pressure mechanism 190, such as a syringe pump 210, which is manually driven or motor-driven as is known in the art. In one embodiment, as shown in FIG. 6, the syringe pump 210 may be driven by an electric motor 211 operatively coupled to controller 145 to allow modulation of the pressure or driving force in combination with the control of energy delivery by emitter 110 from energy source 140.

It may be appreciated that the pressurizing mechanism or pressure source 210 can include any type of mechanism or pump known in the art to actuate the actuator member 175 to move the bone cement in chamber 132. For example, a suitable mechanism can include a piezoelectric element for pumping fluid, an ultrasonic pump element, a compressed air system for creating pressure, a compressed gas cartridge for creating pressure, an electromagnetic pump for creating pressure, an air-hammer system for creating pressure, a mechanism for capturing forces from a phase change in a fluid media, a spring mechanism that may releasably store energy, a spring mechanism and a ratchet, a fluid flow system and a valve, a screw pump, a peristaltic pump, a diaphragm pump, rotodynamic pumps, positive displacement pumps, and combinations thereof.

Referring to FIG. 6, another feature of embodiments of the present disclosure is a remote switch 212 for actuating the pressure mechanism 190. In one embodiment, a cable 214 extends from the controller 145 so that the physician can stand outside of the radiation field created by any imaging system used while treating a vertebra or other bone treatment site. In another embodiment, the switch 212 can be wirelessly connected to the system as is known in the art. In another embodiment (not shown), an elongated cable 214 and switch 212 can be directly coupled to the injector 100 or other component of the system 10.

Figure 7:
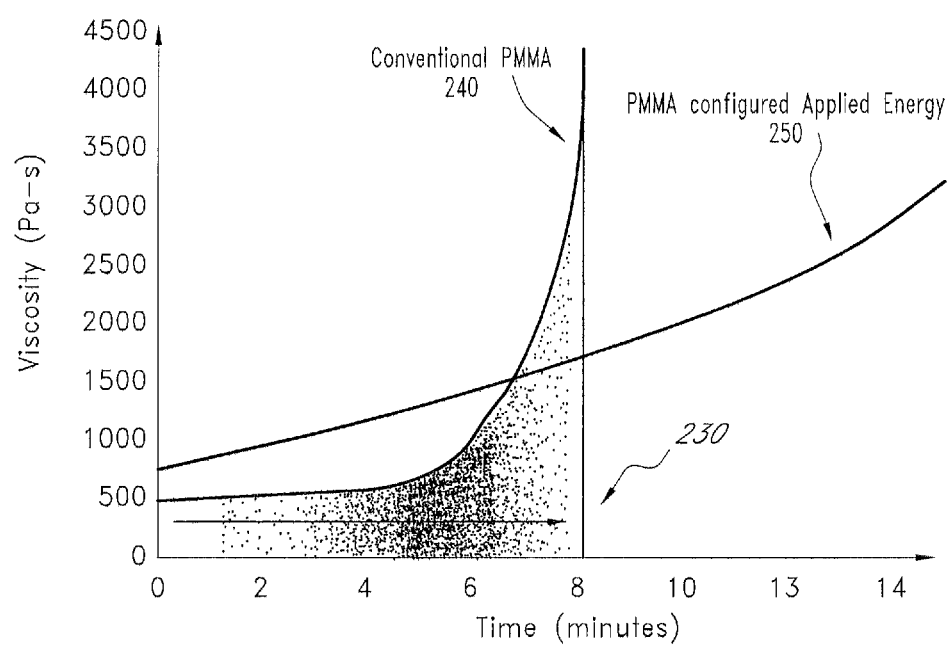
FIG. 7 is chart indicating certain time-viscosity curves for PMMA bone cements.
Figure 8A:
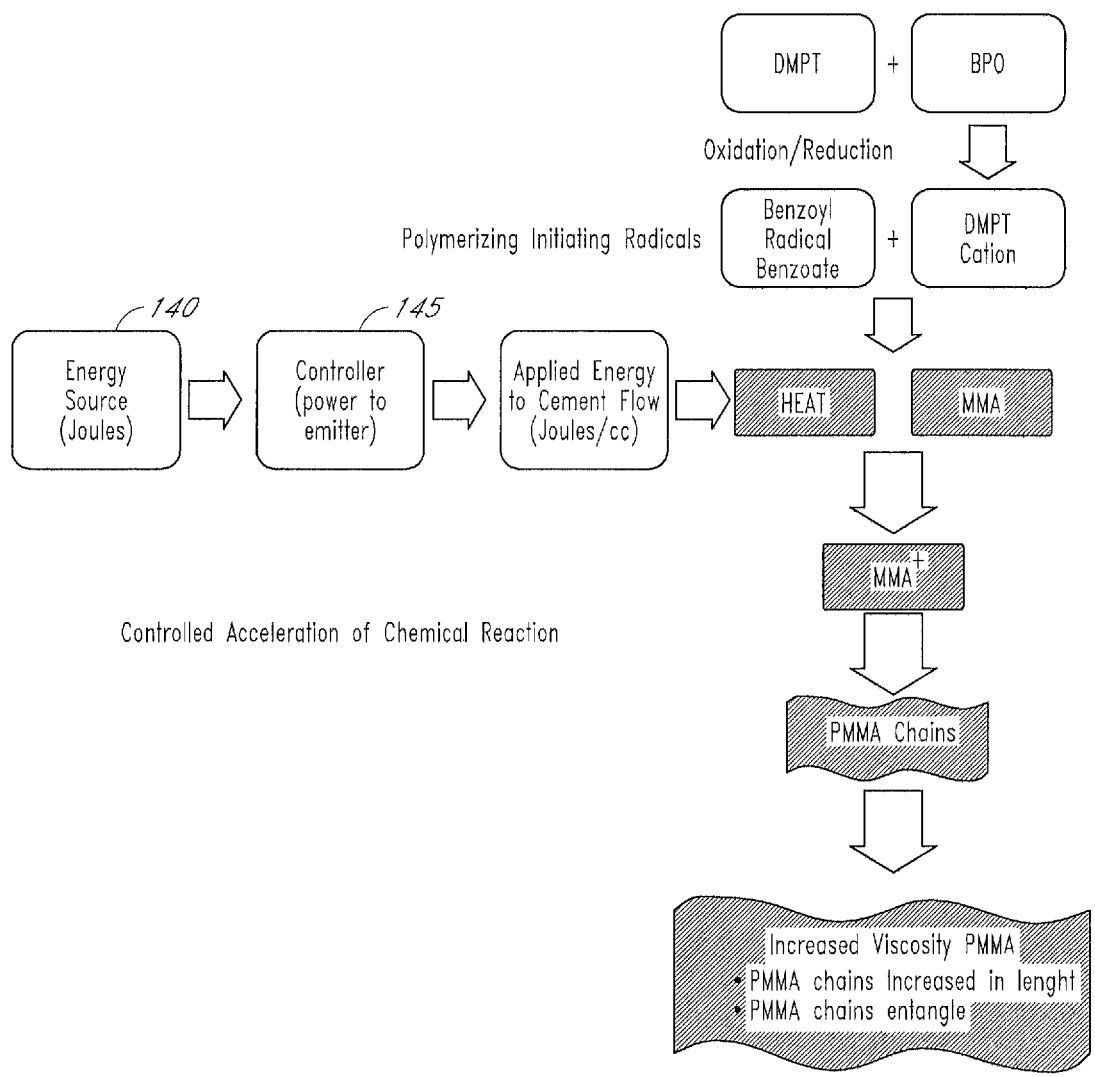
FIG. 8A is diagram indicating a method of utilizing applied energy and an energy-delivery algorithm to accelerate the polymerization of a PMMA bone cement to provide a selected time-viscosity curve.
Figure 8B:
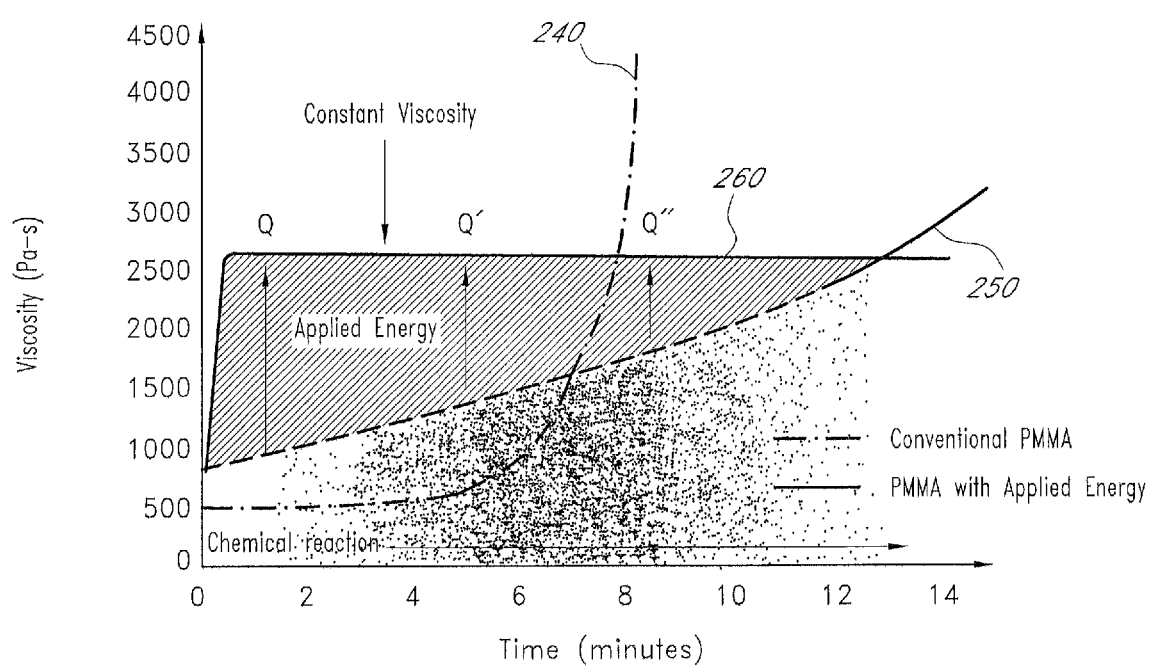
FIG. 8B is a chart indicating a modified time-viscosity curve for a PMMA bone cement of FIG. 7 when modified by applied energy from a thermal energy emitter and a selected energy-delivery algorithm according to an embodiment of the present disclosure.

Now turning to FIGS. 7, 8A and 8B, the figures illustrate certain embodiments of a method wherein controlled application of energy to a bone cement 130 can provide a bone cement with a controlled, on-demand increased viscosity and a controlled set time compared to a prior art bone cement. FIG. 7 depicts a prior art bone cement known in the art, such as a PMMA bone cement, that has a time-viscosity curve 240 where the cement substantially hardens or cures within about 8 to 10 minutes post-mixing. On the horizontal axis of FIGS. 7, and 8B, the time point zero indicates the time at which the mixing of bone cement precursors, such as monomer and polymer components, is approximately completed.

As can be seen in time-viscosity curve 240 for the prior art bone cement, the cement increases in viscosity from about 500 Pa·s to about 750 Pa·s from time zero to about 6 minutes post-mixing. Thereafter, the viscosity of the prior art bone cement increases very rapidly over the time interval from about 6 minutes to 8 minutes post-mixing to a viscosity greater than 4000 Pa·s. A prior art bone cement having the time-viscosity curve 240 in FIG. 7 may be considered to have a fairly high viscosity for injection in the range of about 500 Pa·s. At this viscosity range, however, the bone cement can still have flow characteristics that result in extravasation.

Still referring to FIG. 7, it can be understood that the curing reaction of the bone cement involves an exothermic chemical reaction that initiates a polymerization process that is dictated, at least in part, by the composition of the bone cement precursors, such as one or more of a PMMA polymer, monomer, and initiator. FIG. 7 indicates at 230 the exothermic curing reaction over time as a gradation, where, the lighter gradation region indicates a lesser degree of chemical reaction and heat and the darker gradation region indicates a greater degree of chemical reaction and heat leading to more rapid polymerization of the bone cement precursors.

Now turning to FIG. 8A, the block diagram illustrates an embodiment of a method of utilizing applied energy and an energy-delivery algorithm to accelerate the polymerization of a PMMA bone cement to provide a selected time-viscosity curve as shown in FIG. 8B. In FIGS. 7 and 8B, it can be seen that the time-viscosity curve 250 of one embodiment of a bone cement can have an initial viscosity is in the range of about 750 Pa·s at about time zero post-mixing and thereafter the viscosity increases in a more linear manner over about 10 to 14 minutes post-mixing than the prior art bone cements depicted with curve 240. This embodiment of bone cement that can provide a time-viscosity curve 250 as in FIGS. 7 and 8B, may include a PMMA cement composition as described in U.S. Provisional Application No. 60/899,487 filed on Feb. 5, 2007, titled Bone Treatment Systems and Methods, and U.S. application Ser. No. 12/024,969, filed on Feb. 5, 2008, titled Bone Treatment Systems and Methods, which are each incorporated herein by this reference in their entirety. As can be seen in FIG. 8B, the bone cement 130, or more particularly, the mixing of the cement precursors includes a first curing reaction source for curing the bone cement as described above and can result in the predetermined exothermic curing reaction post-mixing that is indicated by the gradations of reaction under the time-viscosity curve 250.

Still referring to FIG. 8B, the chart illustrates a PMMA bone cement with time-viscosity curve 250 together with a modified time-viscosity curve 260. The modified time-viscosity curve may be provided by the application of energy employing an embodiment of the system 10 of the present disclosure, as depicted in FIGS. 1 and 4-6. In other words, FIG. 8B illustrates one embodiment of the present disclosure, where the bone cement 130 undergoes a curing process (i.e., the time-viscosity curve 250) owing to self-heating of the composition as components of the bone cement composition react with each other. This curing process may be further influenced by the applied energy from energy source 140, controller 145 and emitter 110 to provide the modified time-viscosity curve 260 for cement injection into a bone in order to prevent extravasation.

As can be understood from FIG. 8B, the modulation of applied energy over time from the second curing source or emitter 110, indicated schematically at energy applications Q, Q', and Q", can be provided to complement the thermal energy generated by the exothermic reaction of the bone cement components in order to provide a substantially constant cement viscosity over a selected working time. This aspect of embodiments of the present disclosure allows, for the first time, the provision of bone cements having a controlled, and substantially constant, viscosity that is selected so as to inhibit extravasation.

The bone cement 130 and system 10 of embodiments of the present disclosure are therefore notable in that a typical treatment of a vertebral compression fracture (VCF) requires cement injection over a period of several minutes, for example from about 2 to 10 minutes or about 2 to 6 minutes, or about 2 to 4 minutes. The physician typically injects a small amount of bone cement, for example, about 1 to 2 cc, then pauses cement injection for the purpose of imaging the injected cement to check for extravasation, then injects additional cement and then images, etc. The steps of injecting and imaging may be repeated from about 2 to 10 times or more, wherein the complete treatment interval can take about 4 to 6 minutes or more. It can be easily understood that a cement with a working time of at least about 5-6 minutes is needed for a typical treatment of a VCF, otherwise the first batch of cement may be too advanced in the curing process (see curve 240 in FIG. 7) and a second batch of cement may need to be mixed. In embodiments of the cement 130 and system 10 of the present disclosure, however, as indicated in FIG. 8B at 260, the cement viscosity can be approximately constant, thus providing a very long working time of about 8-10 minutes or more.

It should be appreciated that, in the chart of FIG. 8B, the contribution to bone cement curing owing to self-heating of the bone cement composition and applied energy are indicated by shaded areas below curves 250 and 260. This graphic representation, however, is for conceptual purposes only, as the vertical axis measures viscosity in Pa·s. The actual applied energy, indicated at Q to Q", may be determined by analysis of the actual polymerization reaction time of a selected bone cement composition at a selected ambient temperature and atmospheric pressure.

Thus, in one embodiment of the present disclosure, the bone cement system includes: a first energy source and a second energy source, different from one another, that facilitate a curing reaction occurring within a bone cement. The first energy source includes heat generated by an exothermic curing reaction resulting from mixture of bone cement precursor components. The second energy source includes thermal energy introduced into the bone cement by a thermal energy emitter 110 that may provide a selected amount of energy to the bone cement. The system further includes a controller 145 that may modulate the thermal energy provided to the bone cement composition by the thermal energy emitter 110. In this manner, the curing reaction of the bone cement composition may be controlled over a selected working time. It can be understood from U.S. Provisional Application No. 60/899,487 and U.S. application Ser. No. 12/024,969, that PMMA cement compositions can be created to provide highly-extended working times.

The benefits of such viscosity control may be observed in FIGS. 8C and 8D, which, respectively, are images of a PMMA bone cement exiting an injector without applied energy and the same PMMA bone cement exiting an injector as modified by applied energy according to one embodiment of energy-delivery algorithm. The bone cement emerging from the injector without the benefit of applied energy is of relatively low viscosity, as evidenced by the ease with which the bone cement is deformed by the force of gravity. Such behavior indicates the bone cement of FIG. 8C may be prone to extravasation. In contrast, the bone cement modified by applied energy of high viscosity, as evidenced by its accumulation about the end of the injector. Such behavior indicates that the bone cement of FIG. 8D is not prone to extravasation.

Figure 9:
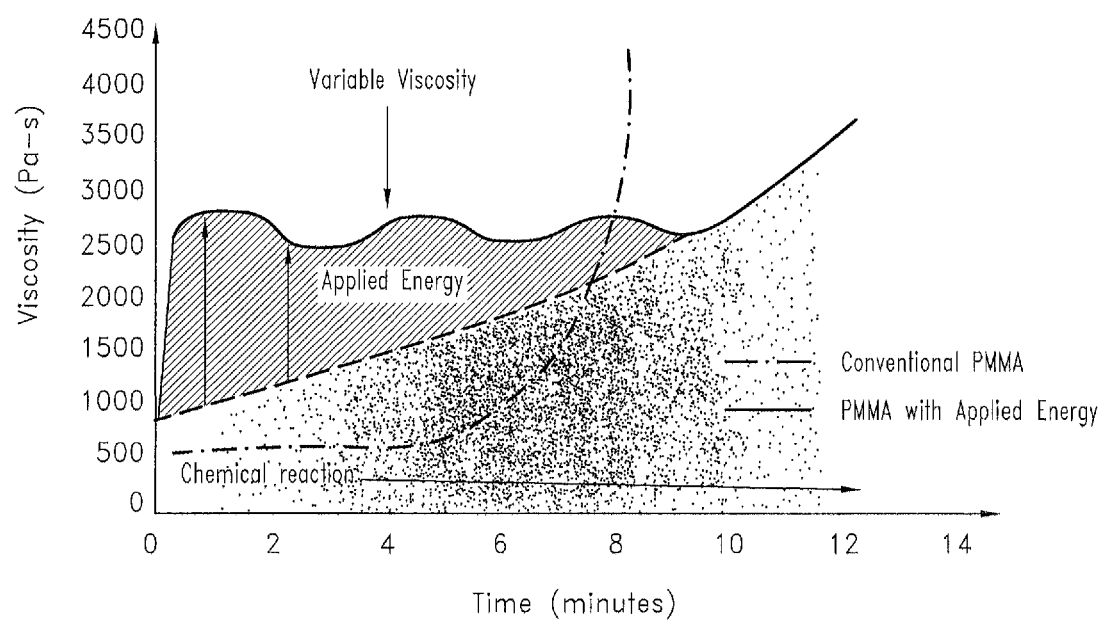
FIG. 9 is chart indicating another modified time-viscosity curve for the PMMA bone cement of FIGS. 7 and 8A when modified by applied energy using an alternative energy-delivery algorithm.

In another embodiment, referring to FIG. 9, the controller 145 may also allow the physician to select an energy-delivery algorithm in the controller 145 to provide a variable viscosity. For example, an algorithm could provide increases and decreases in cement viscosity as the cement exits the injector following the application of energy to the cement flow. Beneficially, such algorithms may provide substantially automated control of the application of energy to the composition by the system 10.

In another embodiment, a bone treatment system 10 may be provided that employs algorithms for modulating energy applied to the bone cement system 130. The bone treatment system 130 may include a bone cement injector system, a thermal energy emitter 110 that may deliver energy to bone cement flowing through the injector system, and a controller. The controller 145 may include hardware and/or software for implementing one or more algorithms for modulating applied energy from the emitter 110 to bone cement flow. The energy-delivery algorithms may be further employed to increase the applied energy from about zero to a selected value at a rate that inhibits vaporization of at least a portion of a monomer portion of the bone cement 130.

In another embodiment, a controller 145 can enable a physician to select a bone cement viscosity using a selector mechanism operatively connected to the controller 145. In certain embodiments, the selector mechanism can initiate one or more of the energy-delivery algorithms. In some embodiments, the physician can select among a plurality of substantially constant viscosities that can be delivered over a working time. Examples of ranges of such viscosities may include less than about 1,000 Pa·s and greater than about 1,500 Pa·s. It should be appreciated that, in certain embodiments, from two to six or more such selections can be enabled by the controller 145, with each selection being a viscosity range useful for a particular purpose, such as about 1,000 Pa·s for treating more dense bone when extravasation is of a lesser concern, or between about 4,000 Pa·s and 6,000 Pa·s for treatment of a vertebral fracture to prevent extravasation and to apply forces to vertebral endplates to reduce the fracture.

In order to facilitate energy application to the bone cement composition in a repeatable manner, the system 10 may further include a temperature sensor 272 disposed in a mixing device or assembly 275 (see FIG. 6). The mixing assembly 275 may include any container that receives bone cement precursors for mixing before placement of the mixed cement in the bone cement source 115. In certain embodiments, the temperature sensor 272 may be placed in the cement mixing assembly 275 because cement may be stored in a hospital in an environment having a lower or higher temperature than the operating room, which may affect the time-viscosity curve of the cement. The temperature sensor 272 can be operatively coupled to the controller 145 by a cable or a wireless transmitter system. In certain embodiments, the sensor 272 may be unitary with the mixing assembly 275 and disposable. In alternative embodiments, the sensor 272 can be reusable and detachable from the mixing assembly 275.

In another embodiment, still referring to FIG. 6, a temperature sensor 276 may be operatively connected to one or more packages 280 of the bone cement precursors to thereby indicate the actual temperature of the cement precursor(s) prior to mixing. Such a temperature sensor 276 may indicate the stored temperature and/or the length of time that such cement precursors have been in the operating room when compared to ambient room temperature measured by sensor 270 in the controller 145. This sensor 276 can include one or more temperature sensors that may include, but are not limited to, thermocouples, or thermochromic inks. The temperature sensors 276 may be further disposed on the surface of the bone cement package 280, allowing for visual identification of the temperature of the cement precursors. In this manner, a doctor or technician may read the temperature of the package 280 and manually input this temperature into the controller 145 to enable automatic adjustment of the energy delivery algorithms. In another embodiment, referring back to FIG. 4, at least one temperature sensor 282 can be located in cement source 115 of the system and/or in a distal portion of the injector component 100 for monitoring cement temperature in a cement flow within the system 10.

In another embodiment, a bone treatment system 10 can include a thermal energy emitter 110 that can deliver energy to a bone cement within the system, a controller 145 that can modulate applied energy from the emitter to control a curing reaction of the cement, and a sensor system operatively coupled to the system 10 for measuring an operational parameter of bone cement 130 within the system 10. In FIG. 6, it can be seen that a sensor of the sensor system may include a temperature sensor, indicated at 270, which is disposed on or in controller 145. The temperature sensor 270 of the controller 145 may allow for input of control algorithms into the system 10 for modulating applied energy from the emitter 110 that are dependent on ambient air temperature in the operating room environment. Such control algorithms may be of significant utility, as the ambient temperature of an operating room can affect the time-viscosity curve of an exothermic PMMA-based bone cement.

In some embodiments, the bone cement system 10, and more particularly, the cement mixing assembly 275 of FIG. 6 may include a sensor, switch, or indication mechanism 285 for indicating an approximate time of initiation of bone cement mixing. Such a sensor or indication mechanism 285 can include any manually-actuated mechanism coupled to the controller, a mechanism that senses the disposition of the cement precursors in the mixing assembly or the actuation of any moveable mixing component of the assembly, and combinations thereof. The system and controller 145 may, in this manner, provide one or more of visual, aural, and/or tactile signals indicating that a selected mixing time interval has been reached. This signal may enable consistent measurement of the time at which mixing of the bone cement is completed, also referred to as the zero post-mixing time, such that the viscosity at this time may be similar in all cases. Beneficially, by precise, consistent measurement of the zero post-mixing time, energy may be properly applied as described above. The system also can include a sensor, switch or indication mechanism 288 that can indicate the termination of bone cement mixing, and thus time zero on a time-viscosity curve as in FIG. 9, which may be used for setting the algorithms in the controller 145 for controlling applied energy and the cement flow rate.

In another embodiment, the bone cement system 10 may include a sensor that measures and indicates the bone cement flow rate within the flow passageway in the injector system 100. In the embodiment of FIG. 6, a motor drive system 211 can drive the cement via the hydraulic system at a substantially constant rate through the injector and emitter 110. As shown, a sensor 290 may be operatively coupled to the motor drive 211 which can measure the force being applied by the drive to cause the desired cement flow through the system, which can in turn be used to sense any tendency for a slow-down in the desired flow rate, for example due to an unanticipated increase in viscosity of the bone cement in the system 10. Upon such sensing, the controller 145 can increase the flow rate or decrease the applied energy from emitter 110 to allow a selected cement viscosity and flow rate from the injector 100 into bone to be maintained.

Bone cements 130, in combination with the system 10 may allow for selected working times of the bone cement. Examples of such working times may include, but are not limited to, at least about 6 minutes, at least about 8 minutes, at least about 10 minutes, at least about 12 minutes, at least about 14 minutes, at least about 16 minutes, at least about 18 minutes, at least about 20 minutes, and at least about 25 minutes.

In some embodiments, a bone treatment system may include: a first and second energy source for causing a controlled curing reaction in a bone cement. The first source may include an exothermic curing reaction which can occur in response to mixing cement precursor components. The second source can include a thermal energy emitter capable of applying energy to the bone cement in order to vary an exothermic curing reaction of the bone cement. The system may further include a controller capable of modulating the applied energy from the emitter to thereby control the exothermic curing reaction over a selected working time. The controller can be capable of modulating applied energy to provide a selected bone cement viscosity over a working time of at least about: 2, 4, 6, 8, 10, 12, 14, 16, 18, 20, and 25 minutes.

In some embodiments the control system 10 may allow for application of energy to a bone cement so as to provide a bone cement that possesses a selected cement viscosity range as it exits the injector outlet 122 over the selected working time. In certain embodiments, the selected viscosity range may include, but is not limited to, about: 600, 800, 1000, 1200, 1400, 1600, 1800, 2000, 2500, 3000, and 4000 Pa·s.

According to some methods, preparing a curable bone cement for injection into a vertebra may be provided. The methods can include: mixing bone cement precursors so as to enable a curing reaction to take place in the bone cement and applying energy to the bone cement from an external source so as to provide energy to the bone cement. The energy applied from the external source may be controlled by a controller in combination with the curing reaction so as to provide a selected cement viscosity.

Embodiments of a method may further include varying the amount of energy applied from the external source in response to a selected length of a post-mixing interval. Embodiments of a method may include varying the amount of applied energy from the external source in response to ambient temperature that is measured by a temperature sensor in the system.

Further, embodiments of a method may include varying the applied energy from the external source in response to a selected injection rate of the bone cement flow through the system 10. Embodiments of a method may include varying the applied energy from the external source so as to provide a bone cement having an injection viscosity of at least about: 500, 1000, 1500, 2000, 3000 and 4000 Pa·s.

In further embodiments the control system may allow for application of energy to a bone cement so as to provide a bone cement that possesses a substantially constant cement viscosity over the selected working time.

In still further embodiments the control system 10 may allow for the application of energy to a bone cement so as to provide a bone cement that possesses a plurality of selected time-viscosity profiles of the cement as it exits the injector 100. For example, the controller 145 and energy emitter 110 may be capable of applying energy to the bone cement in an amount that is sufficient to very rapidly increase the viscosity of the bone cement to a selected viscosity that will inhibit extravasation.

As can be seen in the time-viscosity curve 260 of FIG. 8B, embodiments of the system 10 and the bone cement 130 discussed herein may be employed to provide a bone cement whose viscosity can be elevated to above about 2000 Pa·s within about 15-30 seconds. It can be understood that a method may include utilizing an energy emitter 110 that applies energy to bone cement to controllably increase its viscosity to at least 200 Pa·s, at least 500 Pa·s or at least 1,000 Pa·s in less than 2 minutes or less than 1 minute. Alternatively, a method of bone cement treatment may include utilizing an energy emitter that applies energy to bone cement to controllably increase the viscosity to at least 1,000 Pa·s, at least 1,500 Pa·s, at least 2,000 Pa·s or at least 2,500 Pa·s in less than 2 minutes or less than 1 minute.

In some embodiments, a method of preparing a curable bone cement for injection into a vertebra may be provided that allows a bone cement to exhibit a selected time-viscosity profile. A method may include: mixing bone cement precursors so as to cause a curing reaction characterized by a first time-viscosity profile of the bone cement, actuating an energy controller so as to controllably apply energy to the bone cement from an external energy source so as to cause the bone cement to adopt a second time-viscosity profile, different from the first time-viscosity profile, and injecting the cement characterized by the cement second time-viscosity profile into the vertebra. In some embodiments of this method, the cement viscosity may be at least about 500 Pa·s, at least about 1000 Pa·s, at least about 1500 Pa·s, at least about 2000 Pa·s, at least about 3000 Pa·s, or at least about 4000 Pa·s. Some embodiments of the method may further include actuating the controller to modulate applied energy in response to control signals including, but not limited to, the length of a cement post-mixing interval, the ambient temperature, the bone cement temperature, and rate of bone cement injection into the vertebra.

Figure 10:
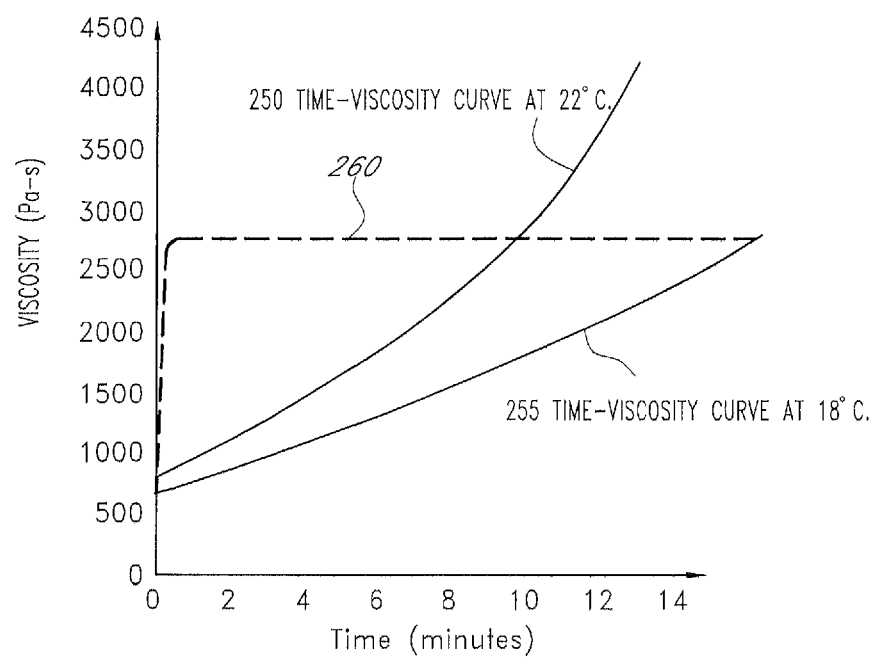
FIG. 10 is a chart indicating time-viscosity curves for an embodiment of PMMA bone cement as in FIG. 8A at different ambient temperatures.

Looking now at FIG. 10, a schematic, graphical representation of the time-viscosity response, 250 and 255, respectively, of an embodiment of the bone cement of FIG. 8A after mixing at ambient temperatures of about 22° C. and 18° C. is shown. It can be seen that different levels of energy may be applied to achieve a similar time-viscosity curve 260. For example, less energy may be applied to bone cement at 22° C. than is applied to the bone cement at 18° C. in order to achieve the time-viscosity response 260, as the higher temperature bone cement, prior to energy application, contains more energy than lower temperature bone cement. Methods may further include providing inputs into the control algorithms for controlling applied energy to cement flows that factor in ambient temperatures.

In one embodiment, the system 10 may be employed in order to provide the bone cement 130 with a working time for polymerizing from an initial state to a selected endpoint of at least about 10 minutes, at least about 12 minutes, at least about 14 minutes, at least about 16 minutes, at least about 18 minutes, at least about 20 minutes, at least about 25 minutes, at least about 30 minutes and at least about 40 minutes, as disclosed in U.S. Provisional Application No. 60/899,487. In an embodiment of the present disclosure, the initial state may include a first selected viscosity range of the bone cement 130 within about 90 to 600 seconds after completion of mixing of the bone cement components. In another embodiment of the disclosure, the selected endpoint of the bone cement 130 may include a second selected viscosity range that substantially inhibits bone cement extravasation. Herein, the terms "polymerization rate" and "working time" may be used alternatively to describe aspects of the time interval over which the cement polymerizes from the initial state to the selected endpoint.

As can be understood from FIGS. 1-6, the energy source 140 may also be capable of applying energy to the bone cement 130 via the emitter 110 and accelerating a polymerization rate of the bone cement 130 by at least about 20%, at least about 30%, at least about 40%, at least about 50%, at least about 60%, at least about 70%, at least about 80%, at least about 90% and at least about 95%, as compared to the polymerization rate achieved absent this application of energy. In another embodiment of the present disclosure, the energy source 140 and controller 145 may be capable of accelerating the polymerization rate of the bone cement 130 to the selected endpoint in less than about 1 second, less than about 5 seconds, less than about 10 seconds, less than about 20 seconds, less than about 30 seconds, less than about 45 seconds, less than about 60 seconds and less than about 2 minutes.

An embodiment of a method of using the system 10 of FIGS. 1-6 to treat a vertebra is also provided. The method can include a first operation of introducing a cement injector needle into a vertebra. The needle may include a flow channel extending from a proximal injector end to a distal injector end possessing a flow outlet. The method may further include a second operation of causing a flow of bone cement from the bone cement source through a flow channel in an energy-delivery component and the injector needle. The method may additionally include applying energy from the energy-delivery component to the flow of bone cement so as to cause a change in the setting rate of the cement so as to reach a selected polymerization endpoint. In this method, the applied energy may accelerate setting of a bone cement before it exits the flow outlet of the injector. The method and the selected polymerization endpoint can advantageously provide a viscosity that substantially prevents cement extravasation following introduction into the vertebra.

Figure 11:
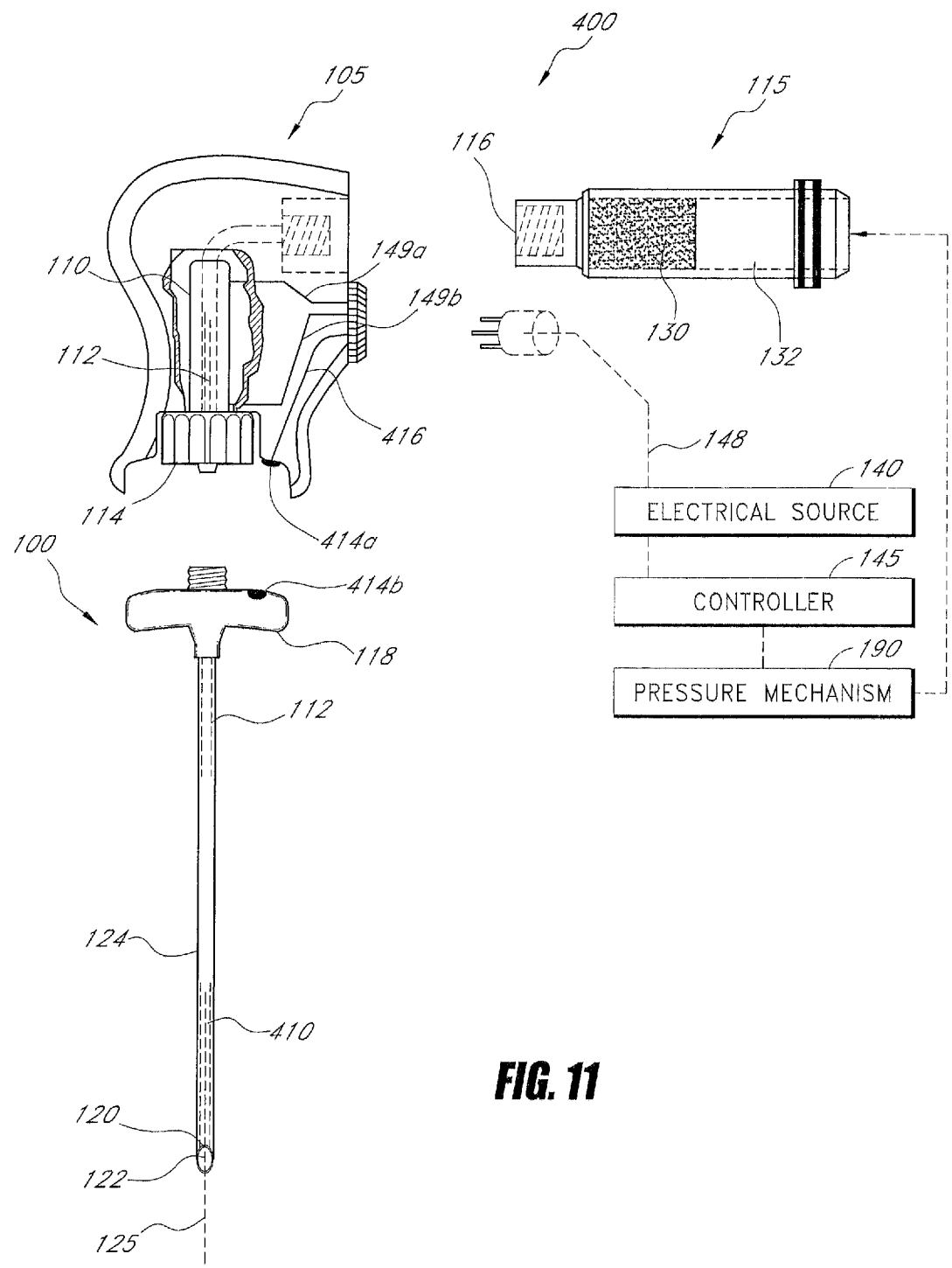
FIG. 11 is a view of another embodiment of a bone cement injection system with some components de-mated from one another wherein the system includes first and second thermal energy emitters.

In another embodiment, referring to FIG. 11, a bone cement system 400 may include a first and a second thermal energy emitter for controlled application of energy to a bone cement flow within the flow passageway 112 of the injector system 100. More particularly, a first emitter 110 is shown disposed in the first handle component 105 as described previously. A second emitter 410 may be disposed in a medial or distal portion of the second extension component 124 of the injector system 100. A controller 145 may be capable of modulating applied energy from the first and second emitters, 110 and 410, to provide a controlled curing reaction of the flow of bone cement 130. In one method of use, the first emitter 110 can apply energy to warm the flow of cement to accelerate polymerization so that the selected flow rate carries the cement 130 to the location of the second emitter 410 at a viscosity of less than about 500 to 1000 Pa·s and, thereafter, the applied energy of the second emitter 410 may increase the viscosity of the bone cement 130 to greater than about 2000 Pa·s. In this manner, the bone cement viscosity within the flow channel 112 can be kept at a level that can be pushed with a low level of pressure and the final viscosity of the bone cement exiting the outlet 122 can be at a relatively high viscosity, for example, at a level capable of fracturing cancellous bone, such as greater than about 2000 Pa·s. It should be recognized that the viscosities given above are examples, the particular viscosity of the flow from the emitters 110 and 410 can depend on many factors, including the cement used, the treatment being performed, etc.

FIG. 11 further illustrates electrical connector components 414a and 414b provided in the interface between the first and second components, 100 and 105. These electrical connector components 414a, 414b can provide an electrical connection from electrical source 140 to the emitter 410 via electrical wires indicated at 416 in the handle portion 105 of the system. It may be appreciated that the second emitter 410 can include a PTCR emitter, as described previously, or any other type of heating element. The heating element can have any length including the entire length of the extension portion 124. In one embodiment, the emitter 110 in handle component 105 has a length of less than about 50 mm and can carry a volume of cement that is less than about: 1.0 cc, 0.8 cc, 0.6 cc, 0.4 and 0.2 cc.

In another embodiment of a method, the energy-delivery emitter 110 may be actuated by the operator from a location outside any imaging field. The cable 214 carrying an actuation switch 212 can be any suitable length, for example about 10 to 15 feet in length (see FIG. 6).

In another embodiment of a method, the energy-delivery emitter 110 may be actuated to apply energy of at least about: 0.01 Watt, 0.05 Watt, 0.10 Watt, 0.50 Watt and 1.0 Watt. In another embodiment of a method, the applied energy may be modulated by a controller 145. In another embodiment of a method, the energy source 140 and controller 145 may be capable of accelerating the polymerization rate of the bone cement 130 to the selected endpoint in less than 1 second, 5 seconds, 10 seconds, 20 seconds, 30 seconds, 45 seconds, 60 seconds and 2 minutes. In another embodiment of a method, the energy source 140 and controller 145 may be capable of applying energy to a bone cement composition 130 for accelerating the polymerization rate of the bone cement 130 by at least about 20%, at least about 30%, at least about 40%, at least about 50%, at least about 60%, at least about 70%, at least about 80%, at least about 90% and at least about 95%, as compared to the polymerization rate absent the applied energy.

In certain embodiments, a method of bone cement injection is also provided. The method includes modulating a rate of bone cement flow in response to a determination of a selected parameter of the cement flow. Examples of the selected parameter may include the flow rate of the bone cement. A method of bone cement injection can further include applying thermal energy to the bone cement and modulating the thermal energy application from an emitter in the injector body to the cement flow. Some methods of bone cement injection can further include modulating the application of energy in response to signals that relate to a selected parameter, such as the flow rate of the cement flow.

In another embodiment, a method of bone cement injection can include (a) providing a bone cement injector body carrying a PTCR (positive temperature coefficient of resistance) material in a flow channel therein, (b) applying a selected level of energy to a bone cement flow through the PTCR material, and (c) utilizing an algorithm that processes impedance values of the PTCR material to determine the bone cement flow rate. The method of bone cement injection may further include modulating a cement injection parameter in response to the processed impedance values. Examples of the cement injection parameter may include, but are not limited to flow rate, pressure, and power applied to the flow.

Another embodiment of a method of bone cement injection can include: (a) providing a bone cement injector body carrying a PTCR material or other thermal energy emitter in a flow channel therein, (b) causing bone cement to flow through the flow channel at a selected cement flow rate by application of a selected level of energy delivery to the cement flow through the emitter, and (c) modulating the selected flow rate and/or energy delivery to maintain a substantially constant impedance value of the emitter material over a cement injection interval. The selected cement injection interval can include at least about 1 minute, at least about 5 minutes, at least about 10 minutes, and at least about 15 minutes.

In another embodiment, a method can modulate the selected flow rate and/or energy delivery to maintain a substantially constant viscosity of bone cement ejected from the injector over a selected cement injection time interval. The time interval may include from about 1 minute to 10 minutes. The system and energy source can be configured for applying energy of at least: 0.01 Watt, 0.05 Watt, 0.10 Watt, 0.50 Watt and 1.0 Watt. In another embodiment, the energy source 140 and controller 145 can be capable of accelerating the polymerization rate of the bone cement to a selected endpoint in less than about: 1 second, 5 seconds, 10 seconds, 20 seconds, 30 seconds, 45 seconds, 60 seconds and 2 minutes.

Another embodiment of a method of bone cement injection may utilize embodiments of the systems 10 and 400 as described above. Such methods may include (a) providing a bone cement injector body with a flow channel extending therethrough from a proximal handle end though a medial portion to a distal end portion having a flow outlet, (b) causing cement flow through the flow channel, and (c) warming the cement flow with an energy emitter in a proximal end or medial portion thereof to initiate or accelerate polymerization of the cement of the cement flow. The method may further include providing a flow rate of the cement flow that ranges from about 0.1 cc/minute to 20 cc/minute, from about 0.2 cc/minute to 10 cc/minute and from about 0.5 cc/minute to 5 cc/minute.

Embodiments of the above-described method of bone cement injection can allow a predetermined cement flow rate to provide a selected interval in which the cement flows are allowed to polymerize in the flow channel downstream from the energy emitter. This method may include providing a selected interval of greater than about 1 second, greater than about 5 seconds, greater than about 10 seconds, greater than about 20 seconds, and greater than about 60 seconds.

The above-described method can utilize an energy emitter that applies energy sufficient to elevate the temperature of the bone cement 130 by at least about 1° C., at least about 2° C. and at least about 5° C. The method of bone cement injection can include utilizing an energy emitter that applies at least about 0.1 Watt of energy to the cement flow, at least about 0.5 Watt of energy to the cement flow, and at least about 1.0 Watt of energy to the cement flow. The method may include adjustment of the flow rate of the bone cement flow in intervals by controller 145, or being continuously adjusted by a controller 145.

In another embodiment of a method, a bone cement injection system as described herein, can utilize a controller 145 and algorithms for applying energy to bone cement flows to allow the bone cement 130 exiting the injector to possess a selected temperature that is higher than the ambient temperature of the injector. This ability reflects the fact that polymerization has been accelerated, thus reducing the amount of total heat released into bone. More particularly, the method can include injecting a settable bone cement into bone after mixing a first component and a second component of the bone cement, thereby initiating a chemical reaction to initiate setting of the bone cement, accelerating the polymerization with applied energy from an external source, and ejecting the bone cement from an injector portion positioned in bone. The bone cement, upon ejection, may possess a temperature greater than ambient temperature of the injector. The method can further include ejecting the bone cement from a terminal portion of an injector positioned in bone at a temperature of at least about: 28° C., 30° C., 32° C., 34° C., 36° C., 38° C., 40° C., 42° C., 44° C., 46° C., 48° C., 50° C., 52° C., 54° C., 56° C., 58° C., 60° C., 62° C., 64° C., 66° C., 68° C., 70° C., 72° C., 74° C., 76° C., 78° C. and 80° C.

In another embodiment, a method of injecting a bone cement into bone can include mixing first and second bone cement components, thereby causing an exothermic chemical reaction which results in a thermal energy release. The method may further include actuating an injector control system capable of controlling the temperature of the bone cement before the bone cement contacts bone. In general, the actuating step can include (i) controlling the flow rate of the bone cement within a flow passageway of an injector system, (ii) controlling the application of energy to the bone cement from an emitter operatively coupled to an energy source, and (iii) controlling the driving force applied to the flow of bone cement which may benefit from adjustment based on the bone cement viscosity.

The actuating step can also include sensing an operating parameter of the bone cement flow to which the controller is responsive. The operating parameter can include the bone cement flow rate, the bone cement temperature, the driving force applied to the cement flow, the energy applied to the cement from an emitter coupled to an energy source and cement viscosity and environmental conditions, such as temperature and humidity in the environment ambient to the injector system. Thus, the controller 145 can be capable of modulating the flow rate, modulating the applied energy, and/or modulating the driving force in response to sensing any one or more of the above operating parameters.

In another embodiment, a method of injecting a bone cement is provided. The method can include mixing first and second bone cement components so as to cause an exothermic chemical reaction that results in a thermal energy release. The method can also include actuating an injector control system which is capable of controlling the amount of thermal energy released from the cement before the bone cement contacts bone tissue to thereby reduce the thermal energy released into the bone.

The thermal energy released from the cement may be directly related to the level of polymerization acceleration from the applied energy, as well as the dwell time of the cement within the flow channel before the cement exits the outlet in a terminal portion of the injector. The dwell time of the cement in the flow channel can be controlled by controller 145 as described above, where at least one of the flow rate and driving force applied to the cement flow can be modulated. In the system embodied in FIGS. 1-6, the application of energy by emitter 110 in component 105 can provide for a dwell time within the flow channel 112 before exiting outlet 122 for a flow interval of at least about: 5 seconds, 10 seconds, 20 seconds, 30 seconds, 40 seconds and 60 seconds. This method of conditioning and injecting bone cement can allow a thermal energy release from the bone cement before the bone cement contacts bone of at least about 10%, at least about 15%, at least about 20%, at least about 25%, at least about 30%, at least about 35%, at least about 40%, at least about 45% and at least about 50%.

In another embodiment, it can be understood that the systems and methods disclosed herein may be further employed in order to control the amount of thermal energy released from the bone cement before the cement contacts bone tissue to thus reduce the amount of thermal energy released into the bone.

For example, in one embodiment, a method of injecting a bone cement can control the amount of thermal energy released by the bone cement before the bone cement contacts bone tissue. The method includes controlling an injector control system that is capable of controlling the rate of chemical reaction before the bone cement contacts bone tissue. The reaction rate can be adjusted by the controller such that the maximum composition temperature is reached when the cement is within the flow channel of the injector system, prior to reaching the bone tissue. Beneficially, in this manner, the amount of total thermal energy released by the bone cement is released while the bone cement is still within the flow channel of the injector system, before the bone cement contacts the bone tissue. This method substantially reduces the amount of thermal energy which is released by the bone cement into the bone tissue.

In another method of injecting bone cement, the actuating step can include allowing at least about 10% of the total thermal energy released from a bone cement to be released while the bone cement flows within the injector system. In certain embodiments, such energy release may be accomplished by providing a mean cement flow rate of at least about 0.1 cc/min, at least about 0.5 cc/min, at least about 1.0 cc/min, at least about 1.5 cc/min, at least about 2.0 cc/min and at least about 2.5 cc/min during heating within the bone cement injector. The method may further include maintaining the bone cement within the cannula for at least about 20 seconds after being heated.

In another method, the actuating step can allow at least about 10% of the total thermal energy released from a bone cement to flow over a flow distance within the flow channel 112 of the injector system, of at least about 5 mm, at least about 10 mm, at least about 20 mm, at least about 30 mm, at least about 40 mm, at least about 50 mm, at least about 60 mm, at least about 70 mm, at least about 80 mm, at least about 90 mm and at least about 100 mm.

In certain embodiments, the methods described above can apply energy to a selected volume of a bone cement mixture. A selected amount of thermal energy from the exothermic reaction of the bone cement components may be released within the flow channel so as to inhibit a selected portion of the thermal energy from reaching a patient's bones. Beneficially, in this manner, a reduction in the thermal effects in the bone due to introduction of the bone cement within the bone may be achieved. Embodiments of the method can include selecting first and second bone cement components, or precursors, that result in a peak temperature of the bone cement composition during curing of less than about: 75° C., 70° C., 65° C. and 60° C. Embodiments of such bone cements may include those bone cements described herein. In certain embodiments, the injected volume subjected to the accelerated chemical reaction releases less thermal energy than a cement mixture not subjected to the accelerated chemical reaction, wherein the release is at least about: 10%, 20%, 30%, 40% and 50% less thermal energy release than a cement mixture not subjected to the accelerated chemical reaction.

Thus, from the above disclosure, it can be understood that some embodiments of bone cement injection systems can include first and second bone cement components, or precursors, that, upon mixing, result in a chemical reaction that sets the cement mixture. The bone cement injection system can further include an injector system that may include a drive system for inducing flow of the cement mixture through the system and into bone. The bone cement injection system can further include an energy emitter for applying energy to the cement mixture in the injector system to thereby accelerate the chemical reaction between the first and second bone cement components therein. The bone cement injection system may also include a controller, operatively coupled to at least one of the drive system and energy emitter, for controlling the acceleration of the chemical reaction in the bone cement. In one embodiment, the first and second bone cement components, or precursors, may possess a post-mixing peak temperature of less than about: 75° C., 70° C., 65° C. and 60° C. The drive system and controller may further be capable of controllably applying a driving force to the cement mixture in the injector system of at least about: 500 psi, 1,000 psi, 1,500 psi, 2,000 psi, 2,500 psi, 3,000 psi, 3,500 psi, 4,000 psi, 4,500 psi and 5,000 psi.

In one embodiment, the drive system and controller can be capable of controllably maintaining a substantially constant flow rate of the cement mixture. Examples of the flow rate control may include, but are not limited to, flow rate variations that are within less than about: 1% variation; 5% variation; 10% variation and 15% variation.

In one embodiment, the drive system and controller can be capable of controlling a mean cement mixture flow rate. The mean cement flow rate may include at least about 0.1 cc/min, at least about 0.5 cc/min, at least about 1.0 cc/min, at least about 1.5 cc/min, at least about 2.0 cc/min and at least about 2.5 cc/min.

The energy emitter and controller may further be capable of controllably applying energy to the cement mixture. In certain embodiments the controller may provide at least about: 20 joules/cc, 40 joules/cc, 60 joules/cc, 80 joules/cc, 100 joules/cc, 120 joules/cc, 140 joules/cc, 160 joules/cc and 180 joules/cc.

In certain embodiments, a bone cement injection system can include an energy emitter and controller capable of providing a dynamic or a pre-programmed adjustment of applied energy to the cement mixture in response to a signal indicative of the flow rate of the cement mixture. The signal, in certain embodiments, may include a feedback signal to the controller 145 indicative of at least one of the temperature of the cement mixture, the viscosity of the cement mixture, the flow rate of the cement mixture and the driving force applied to the cement mixture, at least one environmental condition and combinations thereof.

Further embodiments of the present disclosure relate to bone cement compositions and formulations for use in the bone cement delivery systems described above. The bone cement formulations can provide for an extended working time, since the viscosity of the bone cement can be altered and increased on demand when injected.

Bone cements, such as polymethyl methacrylate (PMMA), have been used in orthopedic procedures for several decades, with initial use in the field of anchoring endoprostheses in a bone. For example, skeletal joints, such as in the hip, have been replaced with a prosthetic joint. About one million joint replacement operations are performed each year in the U.S. Frequently, the prosthetic joint may be cemented into the bone using an acrylic bone cement, such as PMMA. In recent years, bone cements also have been widely used in vertebroplasty procedures where the cement is injected into a fractured vertebra to stabilize the fracture and eliminate micromotion that causes pain.

Polymethyl methacrylate bone cement, prior to injection, can include a powder component and a liquid monomer component. The powder component can include granules of methyl methacrylate or polymethyl methacrylate, an X-ray contrast agent and a radical initiator. Typically, barium sulfate or zirconium dioxide is used as an X-ray contrast agent. Benzoyl peroxide (BPO) is typically used as radical initiator. The liquid monomer component typically consists of liquid methyl methacrylate (MMI), an activator, such as N,N-dimethyl-p-toluidine (DMPT) and a stabilizer, such as hydroquinone (HQ). Prior to injecting PMMA bone cements, the powder component and the monomer component are mixed and thereafter the bone cement hardens within several minutes following radical polymerization of the monomer.

Typical bone cement formulations (including PMMA formulations) used for vertebroplasty have a fairly rapid cement curing time after mixing of the powder and liquid components. This allows the physician to spend less time waiting for the cement to increase in viscosity prior to injection. Further, the higher viscosity cement is less prone to unwanted extravasation which can cause serious complications. The disadvantage of such current formulations is that the "working time" of the cement is relatively short—for example about 5 to 8 minutes—in which the cement is within a selected viscosity range that allows for reasonably low injection pressures while still being fairly viscous to help limit cement extravasation. In some bone cement formulations, the viscosity ranges between approximately 50 to 500 N s/m$^2$ and is measured according to ASTM standard F451, "Standard Specification for Acrylic Bone Cement," which is hereby incorporated by reference in its entirety.

In some embodiments, a bone cement provides a formulation adapted for use with the cement injectors and energy delivery systems described above. These formulations are distinct from conventional formulations and have greatly extended working times for use in vertebroplasty procedures with the "on-demand" viscosity control methods and apparatus disclosed herein and in applications listed and incorporated by reference above.

In some embodiments, a bone cement provides a formulation adapted for injection into a patient's body, wherein the setting time is about 25 minutes or more, more preferably about 30 minutes or more, more preferably about 35 minutes or more, and even more preferably about 40 minutes or more. Setting time is measured in accordance with ASTM standard F451.

In some embodiments, a bone cement, prior to mixing and setting, includes a powder component and a liquid component. The powder component may include a PMMA that is about 64% to 75% by weight based on overall weight of the powder component. In this formulation, an X-ray contrast medium may be further provided in a concentration less than about 50 wt. %, such as about 25 to 35 wt. %, and about 27% to 32 wt. % based on overall weight of the powder component. The X-ray contrast medium, in one embodiment, may include barium sulfate (BaSO$_4$) or zirconium dioxide (ZrO$_2$). In one embodiment, the formulation may further include BPO that is about 0.4% to 0.8% by weight based on overall weight of the powder component. In another embodiment, the BPO is less than about 0.6 wt. %, less than about 0.4 wt. % and less than about 0.2 wt. % based on overall weight of the powder component. In such formulations, the liquid component may include MMA that is greater than about 99% by weight based on overall weight of the liquid component. In such formulations, the liquid component may also include DMPT that is less than about 1% by weight based on overall weight of the liquid component. In such formulations, the liquid component may also include hydroquinone that ranges between about 30 and 120 ppm of the liquid component. In such formulations, the liquid weight/powder weight ratio may be equal to or greater than about 0.4. In such formulations, the PMMA may include particles having a mean diameter ranging from about 25 microns to 200 microns or ranging from about 50 microns to 100 microns.

Figure 12:
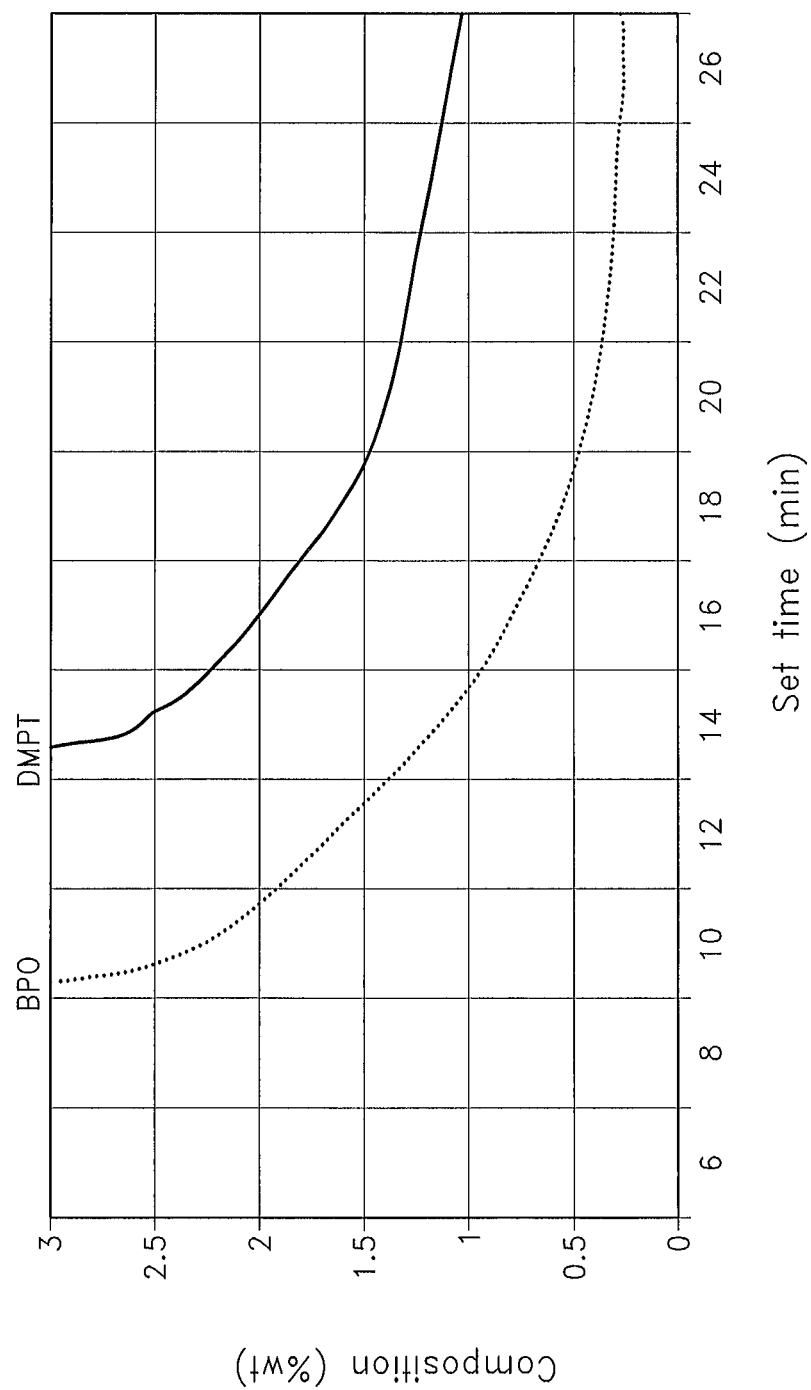
FIG. 12 is a plot illustrating setting time as a function of the concentration of BPO and DMPT present within embodiments of a bone cement composition.

In certain embodiments, the concentrations of benzoyl peroxide and DMPT may be varied in order to adjust setting times. Studies examining the influence of bone cement concentration on setting times (FIG. 12) have demonstrated that, in bone cements comprising BPO and DMPT, increases in BPO and DMPT concentration increase the set time of the bone cement. The data further illustrate that, of the two bone cement constituents, BPO may exert a greater rate of effect on set time than does DMPT. Thus, in certain embodiments of a bone cement composition, the concentration of BPO, DMPT, and combinations thereof, may be increased within the ranges discussed above so as to increase the setting time of the composition.

The setting time of the cement may also be influenced by applying energy to the bone cement composition. As discussed above, embodiments of the injector system of FIGS. 1-6 & 11 may be configured to deliver energy to the bone cement composition. In certain embodiments, the applied energy may heat the bone cement composition to a selected temperature.

Figure 13:
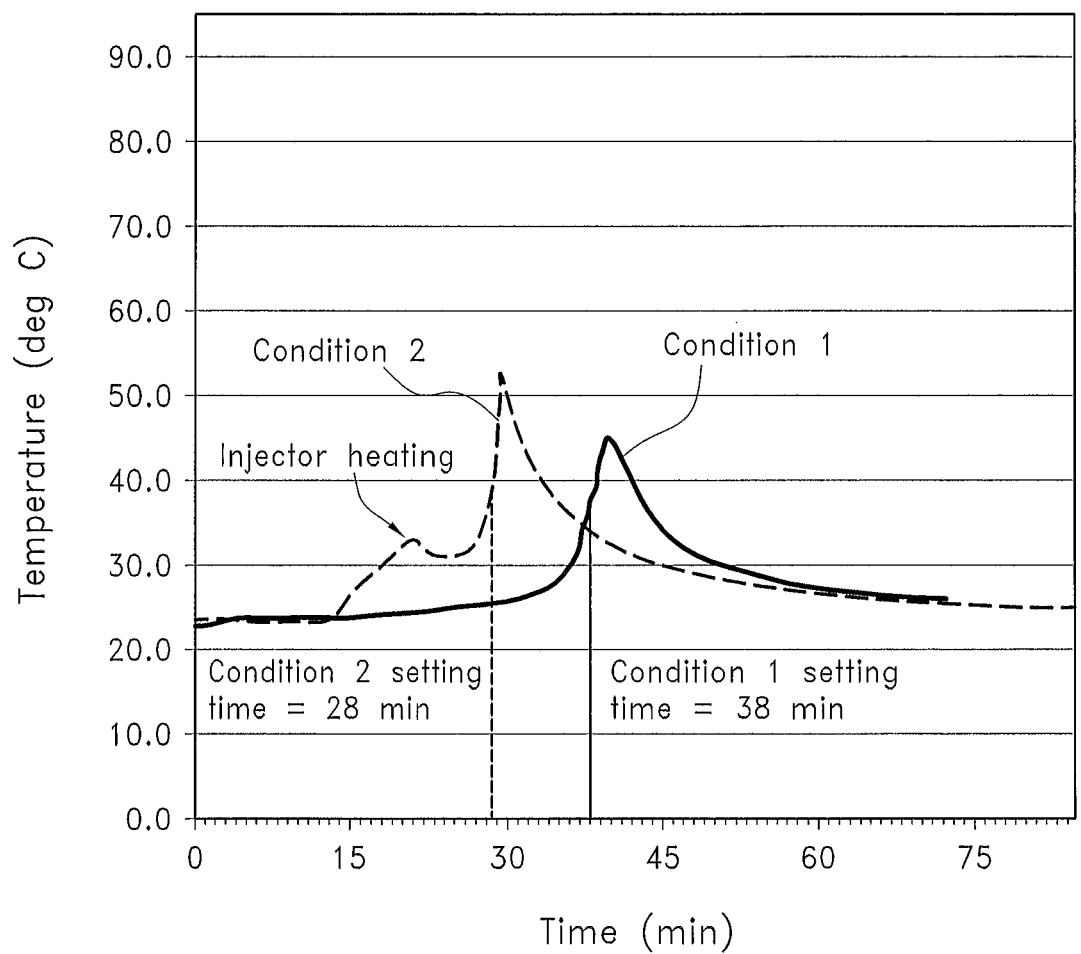
FIG. 13 is a plot illustrating the temperature-time behavior of embodiments of a bone cement composition under conditions where the composition is and is not heated.

FIG. 13 illustrates temperature as a function of time from initial mixing for one embodiment of the bone composition so injected. The solid line of FIG. 13 represents the behavior of the bone cement composition when it is not heated by the injector system, referred to as condition 1. It is observed that, under condition 1, the composition exhibits three regimes. The first regime is low heating rate regime, where the temperature of the composition increases modestly with time. In this regime, the composition begins to slowly self-heat due to the onset of a chemical reaction between at least a portion of its components. The second regime is a high heating rate regime, where the chemical reaction causes the composition temperature to rise sharply. Once the temperature of the composition peaks, the composition enters a third, cooling regime, during which the temperature of the composition decreases back to room temperature.

The dotted line of FIG. 13 represents the behavior of the composition when it is heated by the injector system, referred to as condition 2. In contrast to condition 1, four regimes of behavior are exhibited by the composition under condition 2. The first, low heating rate regime, the second, high heating rate regime, and the third, cooling regime, are again observed. In contrast with condition 1, however, a new, injector heating regime, is observed between the first and second regimes. This new regime exhibits a rapid increase in the composition temperature due to injector heating of the composition. Although the composition temperature is observed to peak and fall towards the end of the duration of this regime, the temperature does not fall back to the same level as observed under condition 1 at about the same time. Therefore, when the second, high heating rate regime is entered, the temperature of the composition under condition 2 is greater than that under condition 1 and the composition temperature rises to a peak temperature which is greater than that achieved under condition 1.

The setting time of the compositions under conditions 1 and 2 can be measured according to ASTM standard F451 and compared to identify changes in setting time between the two conditions. It is observed that the setting time of the composition under condition 1 is approximately 38 minutes, while the setting time of the composition under condition 2 is approximately 28 minutes, a reduction of about 10 minutes. Thus, by heating the bone cement, the setting time of embodiments of the bone cement composition may be reduced.

From the forgoing, then, it can be appreciated that by varying the BPO and/or DMPT concentrations of the bone cement composition, or by heating the bone cement composition, the setting time of the bone cement may be increased or decreased. Furthermore, in certain embodiments, the concentration of BPO and/or DMPT in the bone cement may be varied and the composition may be heated so as to adjust the setting time to a selected value. As discussed above, in certain embodiments, the setting time is selected to be about 25 minutes or more, more preferably about 30 minutes or more, more preferably about 35 minutes or more, and even more preferably about 40 minutes or more.

Figure 14:
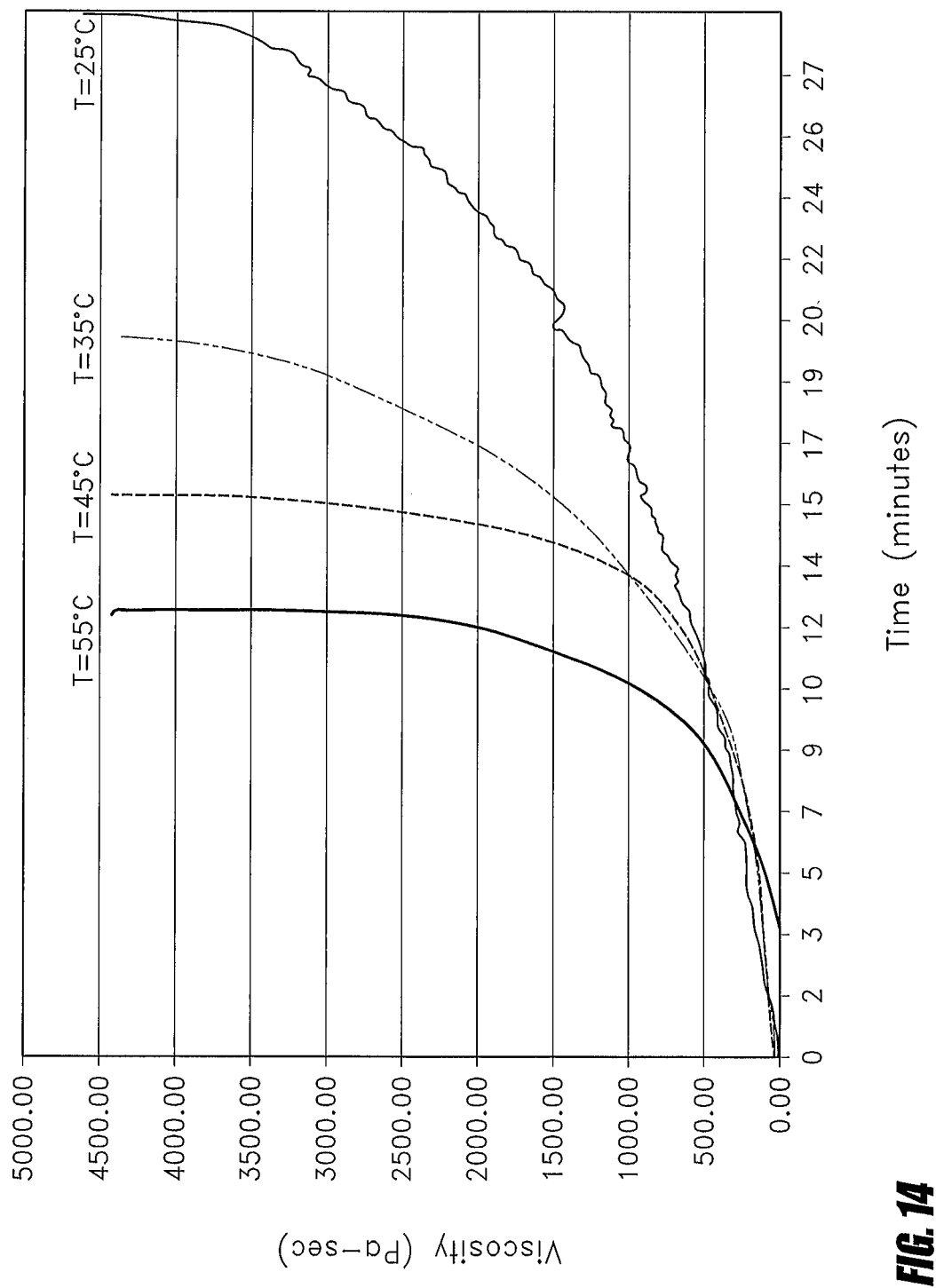
FIG. 14 is a plot illustrating the viscosity-time behavior of embodiments of a bone cement composition heated to temperatures ranging between about 25° C. to 55° C.

Embodiments of a bone cement composition may further be heated using the injector systems described herein in order to alter the viscosity of the composition. FIG. 14 illustrates measurements of viscosity as a function of time for an embodiment of the bone cement compositions heated to temperatures ranging between about 25° C. to 55° C. It may be observed that the bone cement at the lowest temperature, 25° C., exhibits the slowest rate of viscosity increase, while the bone cement at the highest temperature, 55° C., exhibits the highest rate of viscosity increase. Furthermore, at intermediate temperatures, the bone cement exhibits intermediate rates of viscosity increase.

From the behavior of condition 1 in FIG. 13, it can be seen that the peak temperature of the bone cement composition is higher when the cement is heated by the injector system. Furthermore, by adjusting the energy output of the injector system, the temperature to which the bone cement rises may be varied. Thus, embodiments of the injector system may be employed to deliver bone cements having selected levels of viscosity.

In one embodiment, a bone cement has a first component comprising greater than about 99 wt. % methyl methacrylate (MMA), less than about 1 wt. % N,N-dimethyl-p-toluidine (DMPT), and about 30 to 120 ppm hydroquinone on the basis of the total amount of the first component, and a second component comprising a powder component comprising less than about 75 wt. % PMMA, less than about 50 or 32 wt. % of an X-ray contrast medium, and benzoyl peroxide (BPO).

In certain embodiments, the composition may further include less than about 0.4 wt. % (BPO) on the basis of the total weight of the second component. In further embodiments, the composition may include about 0.2 to 0.3 wt. % BPO on the basis of the total weight of the second component. In other embodiments, the second component has less than about 0.2 wt. % benzoyl peroxide (BPO) on the basis of the total weight of the second component, or less than about 0.1 wt. % benzoyl peroxide (BPO) on the basis of the total weight of the second component. In such a formulation, the liquid weight/powder weight ratio may be equal to or greater than about 0.4.

In one embodiment, a bone cement may include a first monomer-carrying component and a second polymer-carrying component, such as the liquid and powder components discussed above. The bone cement mixture, after mixing, may be characterized by having a viscosity of less than about 500 Pa·s at about 18 minutes post-mixing. The bone cement further can be characterized as having a time-viscosity curve slope of less than about 200 Pa·s/minute for at least about 5 minutes after reaching a viscosity of about 500 Pa·s. The bone cement further can be characterized by a post-mixing time-viscosity curve slope of less than 100 Pa·s/minute for at least about 15 minutes, at least about 16 minutes, at least about 17 minutes, at least about 18 minutes, at least about 19 minutes, and at least about 20 minutes.

In one embodiment, a bone cement can include a first monomer-carrying component and a second polymer-carrying component, such as the liquid and powder components discussed above. Post-mixing, the bone cement mixture may be characterized by a time-viscosity curve having a slope of less than about 100 Pa·s/minute until to the mixture reaches a viscosity of about 500 Pa·s. In other embodiments, the bone cement, post-mixing, can be characterized by a time-viscosity curve slope of less than about 100 Pa·s/minute immediately before the mixture reaches a viscosity of about 800 Pa·s. In this context, immediately may refer to a time period less than about 30 seconds. In other embodiments, the bone cement further can be characterized by a time-viscosity curve slope of less than about 100 Pa·s/minute immediately before the mixture reaches a viscosity of about 1000 Pa·s. In other embodiments, the bone cement further can be characterized by a time-viscosity curve slope of less than about 100 Pa·s/minute immediately before the mixture reaches a viscosity of about 1500 Pa·s.

In other embodiments, the bone cement further can be characterized by a time-viscosity curve slope of less than about 200 Pa·s/minute immediately before the mixture reaches a viscosity of about 500 Pa·s. In other embodiments, the bone cement further can be characterized by a time-viscosity curve slope of less than about 200 Pa·s/minute immediately before the mixture achieves a viscosity of about 1000 Pa·s. In other embodiments, the bone cement further can be characterized by a time-viscosity curve slope of less than about 200 Pa·s/minute immediately before the mixture achieves a viscosity of about 1500 Pa·s. In other embodiments, the bone cement further can be characterized by a time-viscosity curve slope of less than 200 Pa·s/minute immediately before the mixture achieves a viscosity of about 2000 Pa·s, about 3000 Pa·s and about 4000 Pa·s.

In one embodiment, a bone cement may include a first monomer-carrying component and a second polymer-carrying component, wherein post-mixing the mixture is characterized by a change of viscosity of less than about 20% over an interval of at least about 5 minutes, at least about 10 minutes, at least about 15 minutes, and at least about 20 minutes. In other embodiments, the mixture may be characterized by a time-viscosity curve having a rate of change less than about 40% over an interval of at least about 5 minutes, at least about 10 minutes, at least about 15 minutes, and at least about 20 minutes.

In one embodiment, the bone cement may include a first monomer-carrying component and a second polymer-carrying component, such as the liquid and powder components discussed above. In certain embodiments, after mixing, the mixture of the first and second components may be characterized as having a viscosity of less than about 100 Pa·s at about 10 minutes post-mixing, less than about 200 Pa·s at about 15 minutes post-mixing, or less than about 500 Pa·s at about 18 minutes post-mixing.

In one embodiment, the bone cement may include a first monomer-carrying component and a second polymer-carrying component, such as the liquid and powder components discussed above. In certain embodiments, after mixing, the mixture may receive applied energy of at least about 20 joules/cc, at least about 40 joules/cc, at least about 60 joules/cc, at least about 80 joules/cc, at least about 100 joules/cc, at least about 120 joules/cc, at least about 140 joules/cc, at least about 160 joules/cc, and at least about 180 joules/cc without substantially setting in an interval of less than about 10 minutes. In other embodiments, the bone cement, after mixing, may possess a viscosity greater than about 500 Pa·s within about 10 seconds, about 30 seconds, about 60 seconds, about 90 seconds, about 120 seconds, about 180 seconds, and about 240 seconds of application of energy from an external source of at least about 60 joules/cc.

In certain embodiments, the cement mixture of the precursors may be characterized by a post-mixing interval in which viscosity is between about 500 Pa·s and 5000 Pa·s, and in which the change of viscosity of less than about 30%/minute. In another embodiment, the settable bone cement includes first and second cement precursors, where the cement mixture of the precursors is characterized by a post-mixing interval in which the viscosity of the mixture is between about 500 Pa·s and 2000 Pa·s, and in which the change of viscosity of the mixture is less than about 20%/minute.

In another embodiment, the settable bone cement includes a first monomer-carrying component and a second polymer-carrying component, such as the liquid and powder components discussed above. In certain embodiments, after mixing the first and second components, the mixture is characterized by a change of viscosity of less than 20%/minute for at least three minutes after reaching about 500 Pa·s, about 1000 Pa·s, about 1500 Pa·s, and about 2000 Pa·s.

In another embodiment, the cement includes a first monomer-carrying component and a second polymer-carrying component, such as the liquid and powder components discussed above. In certain embodiments, after mixing the first and second components, the mixture is characterized by a change of viscosity of less than 30%/minute for at least three minutes after reaching about: 500 Pa·s, 1000 Pa·s, 1500 Pa·s and 2000 Pa·s. In a related embodiment, the cement can include a first monomer-carrying component and a second polymer-carrying component, wherein post-mixing the mixture is characterized by a change of viscosity of less than 40%/minute for at least three minutes after reaching about: 500 Pa·s, 1000 Pa·s, 1500 Pa·s and 2000 Pa·s. In a related embodiment, the cement can include a first monomer-carrying component and a second polymer-carrying component, wherein post-mixing the mixture is characterized by a change of viscosity of less than 30%/minute for at least five minutes after reaching about: 1000 Pa·s, 1500 Pa·s, 2000 Pa·s, 2500 Pa·s, 3000 Pa·s, 3500 Pa·s and 4000 Pa·s.

In a further embodiment, the cement may include a first monomer-carrying component and a second polymer-carrying component, wherein the mixture is characterized by a rate of change of viscosity of less than about 40%/minute for at least five minutes after reaching about 1000 Pa·s, about 1500 Pa·s, about 2000 Pa·s, about 2500 Pa·s, about 3000 Pa·s, about 3500 Pa·s, and about 4000 Pa·s.

In a related embodiment, a cement includes a first monomer-carrying component and a second polymer-carrying component, such as the liquid and powder components discussed above. In certain embodiments, after mixing the first and second components, the mixture is characterized by a change of viscosity of less than about 50%/minute for at least about five minutes after reaching about 1000 Pa·s, about 1500 Pa·s, about 2000 Pa·s, about 2500 Pa·s, about 3000 Pa·s, about 3500 Pa·s, and about 4000 Pa·s.

In another embodiment of the present disclosure, a cement includes a first monomer-carrying component and a second polymer-carrying component, such as the liquid and powder components discussed above. In certain embodiments, after mixing the first and second components, the mixture is characterized by a rate of change of viscosity of less than about 50%/minute after reaching a viscosity of about 5000 Pa·s. In a related embodiment, a cement includes a first monomer-carrying component and a second polymer-carrying component, such as the liquid and powder components discussed above. In certain embodiments, after mixing the first and second components, the mixture is characterized by a rate of change of viscosity of less than about 50%/minute after achieving a viscosity of about 4000 Pa·s. In a related embodiment, a cement includes a first monomer-carrying component and a second polymer-carrying component, such as the liquid and powder components discussed above. In certain embodiments, after mixing the first and second components, the mixture is characterized by a rate of change of viscosity of less than about 50%/minute after achieving a viscosity of about 3000 Pa·s.

In another aspect, a cement can include a first monomer-carrying component and a second polymer-carrying component, wherein post-mixing the mixture is characterized by a rate of change of viscosity of less than 50%/minute for an interval preceding the point in time the mixture achieves about 5000 Pa·s, the interval being at least about: 2, 3, 4, 5, 6 and 8 minutes.

In a related embodiment, a cement includes a first monomer-carrying component and a second polymer-carrying component, wherein the mixture is characterized post-mixing by a rate of change of viscosity of less than about 40%/minute for an interval preceding the point in time the mixture achieves about 5000 Pa·s, the interval being at least about: 2, 3, 4, 5, 6, and 8 minutes.

In a related embodiment, a cement can include a first monomer-carrying component and a second polymer-carrying component, such as the liquid and powder components discussed above. In certain embodiments, after mixing the first and second components, the mixture is characterized by a rate of change of viscosity of less than about 30%/minute for an interval preceding the point in time the mixture achieves about 5000 Pa·s, the interval being at least about: 2, 3, 4, 5, 6, and 8 minutes.

In another embodiment of the present disclosure, a cement includes a first monomer-carrying component and a second polymer-carrying component, such as the liquid and powder components discussed above. In certain embodiments, after mixing the first and second components, the mixture is characterized by a post-mixing interval of at least 4 minutes, 6 minutes, 8 minutes or 10 minutes in the interval preceding the point in time the mixture achieves 3000 Pa·s.

In a related embodiment of the present disclosure, a cement includes a first monomer-carrying component and a second polymer-carrying component, such as the liquid and powder components discussed above. In certain embodiments, after mixing the first and second components, is characterized by a post-mixing interval of at least about 4 minutes, at least about 6 minutes, at least about 8 minutes or at least about 10 minutes in the interval preceding the point in time the mixture achieves at least about 4000 Pa·s.

In a related embodiment of the present disclosure, a cement includes a first monomer-carrying component and a second polymer-carrying component, such as the liquid and powder components discussed above. In certain embodiments, after mixing the first and second components, is characterized by a post-mixing interval of at least about 4 minutes, at least about 6 minutes, at least about 8 minutes or at least about 10 minutes in the interval preceding the point in time the mixture achieves about 5000 Pa·s.

Figure 15:
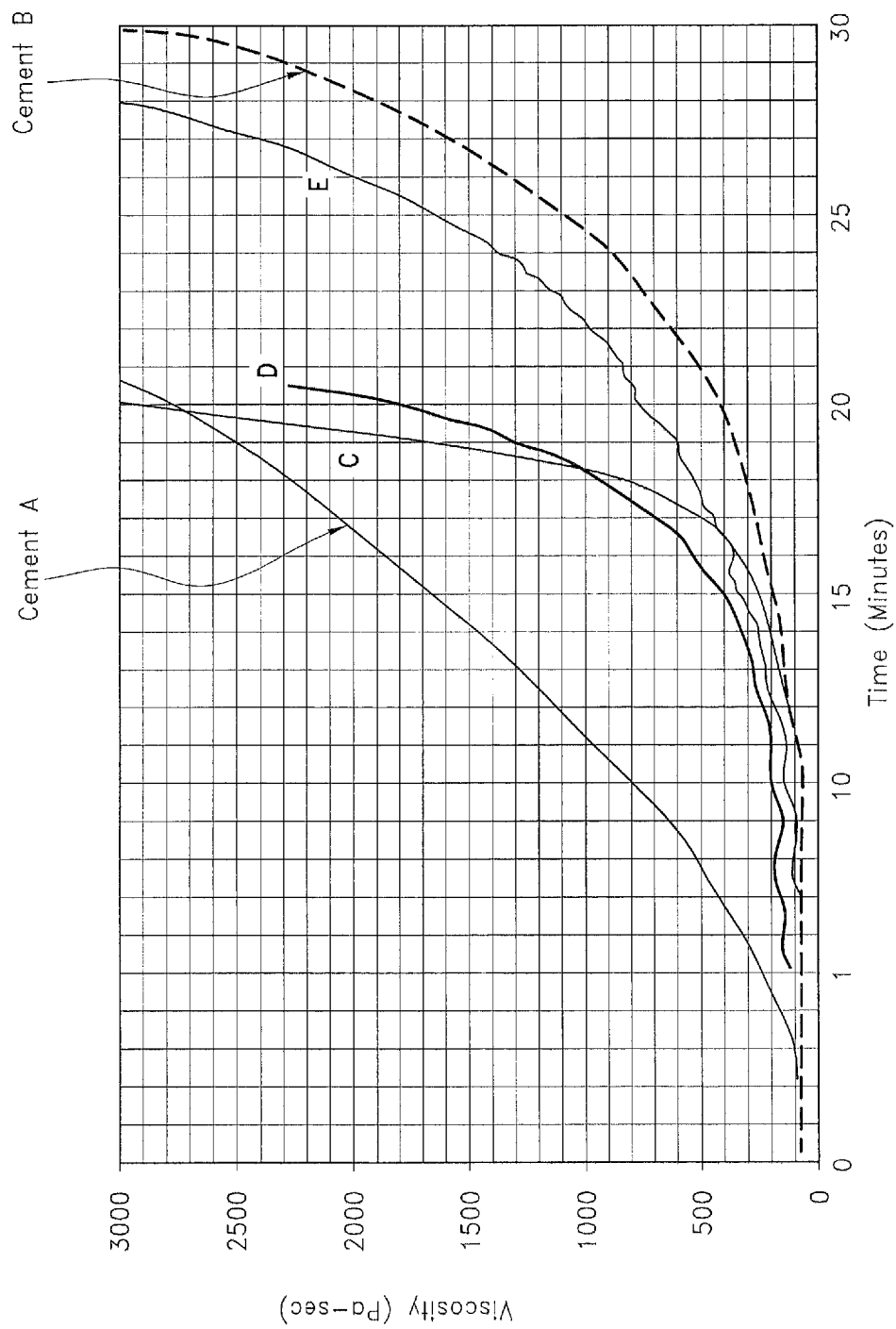
FIG. 15 is a chart indicating time-viscosity curves for two embodiments of PMMA bone cement of this disclosure as well as other commercially available PMMA bone cements.

Now turning FIG. 15, embodiments of bone cement described above can be characterized by the time-viscosity curves of cements A and B, and compared with commercially available cements C, D and E. Cement A is a bone cement composition of the present disclosure having a PMMA to monomer ratio of about 2:1. Cement B is also a cement composition of the present disclosure having a PMMA to monomer ratio of about 2.5:1. Cement C is Mendec Spine bone cement which includes a PMMA to monomer ratio of about 2.1:1. D is DePuy Vertebroplasty cement which includes a PMMA to monomer ratio of about 2.3:1. Cement E is Arthrocare Parallax acrylic resin, which includes a PMMA to monomer ratio of about 2.4:1.

Cement A includes a first monomer-carrying component and a second polymer-carrying component, such as the liquid and powder components discussed above. In certain embodiments, post-mixing, the mixture is characterized by a time-viscosity curve slope of less than about 200 Pa·s/minute until the mixture achieves a viscosity of about 3000 Pa·s. In another cement embodiment, Cement A may include a first monomer-carrying component and a second polymer-carrying component, where, post-mixing, the mixture is characterized by a time-viscosity curve slope of less than about 200 Pa·s/minute until to the mixture achieves a viscosity of about 2500 Pa·s. Bone cement B includes a first monomer-carrying component and a second polymer-carrying component, where, post-mixing, the mixture is characterized by a time-viscosity curve slope of less than about 200 Pa·s/minute for at least about 20 minutes, at least about 25 minutes, and at least about 30 minutes.

Beneficially, as compared to the prior art compositions (C, D, E) each of compositions A and B may be observed to exhibit a relatively long working time before their slope increases significantly. Furthermore, compositions A and B exhibit a more linear slope than the prior art compositions, which indicates that the rate of viscosity change with time is more constant.

In another embodiment of the present disclosure, a settable or curable bone cement is provided that includes two mixable components as described above: a liquid monomer component and a non-liquid component. In this embodiment of bone cement, the non-liquid component may include polymer beads or particles containing an initiator, for example, BPO. The non-liquid component may be capable of providing controlled exposure of the initiator to the liquid monomer over a selected time interval during which the bone cement sets, also referred to as a setting interval of the bone cement. The controlled exposure of the initiator, such as BPO, to the monomer, can provide control over the time-viscosity curve of a bone cement over a working time of the cement.

Embodiments of cement may be used with the systems disclosed herein, including those shown in FIGS. 1-6 & 11, or may be used in a conventional form of vertebroplasty. Further embodiments of the cement may be employed with the systems disclosed herein in order to provide any of the physical properties of the cement discussed herein.

In one embodiment, a settable bone cement may include mixable first and second components, wherein the first component includes greater than about 99 wt. % methyl methacrylate (MMA), and less than about 1 wt. % N,N-dimethyl-p-toluidine (DMPT), about 30 to 120 ppm hydroquinone on the basis of the total amount of the first component, and wherein the second component includes a PMMA component that includes less than about 75 wt. % PMMA, less than about 32 wt. % of an X-ray contrast medium; and a selected wt. % of benzoyl peroxide (BPO) on the basis of the total weight of the second component. More particularly, the PMMA component may includes first and second volumes of polymer beads having first and second amounts of BPO, respectively.

Figure 16:
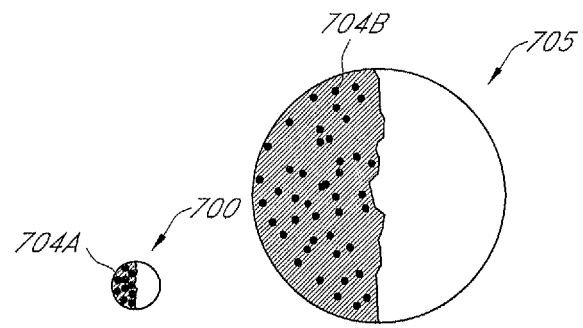
FIG. 16 is a schematic view of polymer beads of an embodiment of bone cement.

In one embodiment of bone cement compositions with controlled exposure of BPO, referring to FIG. 16, the desired differential BPO exposure over the working time of the cement may be provided by polymer beads or particles and having differing BPO configurations integrated therein. FIG. 16 illustrates first polymer beads 700 of the non-liquid component which have a small diameter and include BPO 704A in a higher density when compared to BPO 704B within second polymer beads 705 of the non-liquid component of the cement.

In an embodiment, the first polymer beads 700 can have an average cross section of less than about 100 microns, less than about 80 microns, less than about 60 microns, or less than about 40 microns. The first polymer beads 700 may further include greater than about 0.5 wt. % of BPO, on the basis of the total weight of the non-liquid component. Still referring to FIG. 16, the second polymer beads or particles 705 can have an average cross section of greater than about 40 microns, greater than about 60 microns, greater than about 80 microns, and greater than about 100 microns, with a less than about 0.5 wt. % of BPO, on the basis of the total weight of the non-liquid component. In combination, the first and second polymer beads or particles 700, 705 may include less than about 5.0 wt. % of BPO, on the basis of the total weight of the non-liquid component.

In another embodiment, the PMMA component includes a first volume of polymer beads 700 having greater than about 0.4 wt. % BPO on the basis of the total weight of the PMMA component and the first volume has a mean bead diameter of less than about 100 microns. In this embodiment, the PMMA component may include a second volume of polymer beads 705 having less than about 0.4 wt. % BPO on the basis of the total weight of the PMMA component and the second volume has a mean bead diameter of greater than about 100 microns.

In another embodiment, the bone cement may include a plurality of different PMMA beads of differing sizes, each carrying a BPO. The amount of BPO may be varied, as necessary, between the different PMMA beads. In another embodiment, the mean BPO amount contained within the plurality of beads may range from about 0.3 to 0.6 wt. on the basis of the total weight of the PMMA.

In another embodiment, the PMMA component may include a first volume of polymer beads 700 that has greater than about 0.4 wt. % BPO on the basis of the total weight of the PMMA and the first volume of polymer beads 200 has a mean bead diameter of greater than about 100 microns. Further, the PMMA component may include a second volume of polymer beads 705 having less than about 0.4 wt. % BPO on the basis of the total weight of the PMMA component and the second volume of polymer beads 705 has a mean bead diameter of less than about 100 microns.

Figure 17:
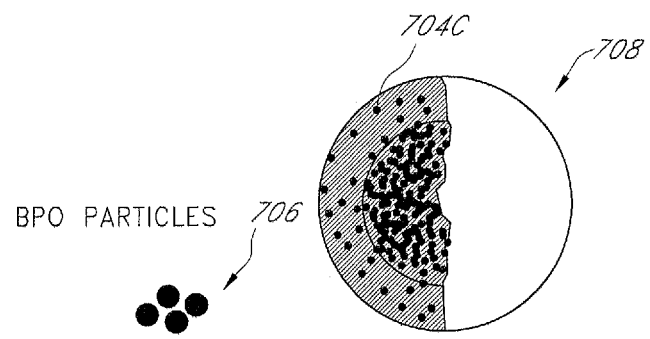
FIG. 17 is a schematic view of polymer beads of another bone cement embodiment.

In another embodiment of bone cement, FIG. 17, the BPO in the non-liquid component may be included in the form of particles 706 of BPO and BPO particles 704C integrated into polymer particles 708. The BPO particles 706 may possess a mean diameter ranging between about 1 to 40 µm and may be present within the non-liquid component in a concentration ranging between about 0.3 to 2 wt. % on the basis of the total weight of the non-liquid component. The BPO particles 704C within the polymer particles 708 may possess a mean diameter ranging between about 0.5 to 5 µm and possess a concentration ranging between about 0.1 to 2 wt. % on the basis of the total weight of the non-liquid component.

In another embodiment, the polymer particles 708 can have regions of differing density of BPO 704C. Examples of densities may include, but are not limited to, about 10,000 to 100,000 particles/cm$^3$ of the polymer particles 708.

In certain embodiments, BPO particles 706 may be further added to the bone cement composition in combination with the polymer particles 708. The BPO particles 706 may possess a mean diameter ranging between about 1 to 40 μm and may be present within the non-liquid component in a concentration ranging between about 0.3 to 2 wt. % on the basis of the total weight of the non-liquid component.

Figure 18:
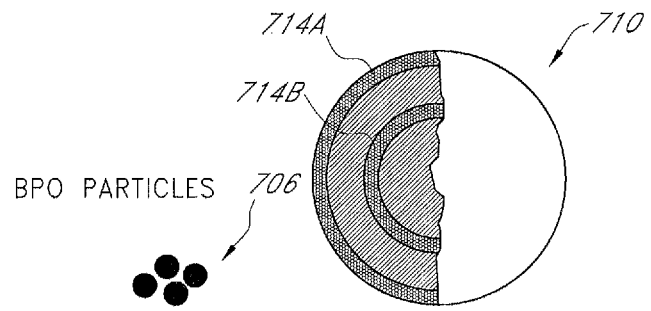
FIG. 18 is a schematic view of polymer beads of a further embodiment of bone cement.

In another embodiment of bone cement, FIG. 18, the BPO configuration in the non-liquid component can include polymer particles 710 comprising layers of BPO. The BPO may be configured as a surface layer 714A which is present on at least a portion of an exterior surface of the polymer particles 710. In a further embodiment, one or more BPO layers 714B may be present within the interior of the polymer particles 710. In an additional embodiment, one or more surface BPO layers 714A may be present upon at least a portion of the surface of the exterior surface of the polymer particles 710 and one or more interior BPO layers 714B may be present within the interior of the polymer particles 710. The interior BPO layers 714B may be positioned at radial distances of about 5 to 80 μm from the center of the polymer particles 710. The BPO surface layers and interior layers 714A, 714B may possess thicknesses ranging between about 0.5 to 30 μm. In alternative embodiments, the volume of BPO surface coatings and interior layers 714A, 714B may range between about $1 \times 10^{-10}$ to $1 \times 10^{-4}$ cm$^3$.

In certain embodiments, BPO particles 706 may be further added to the bone cement composition in combination with the polymer particles 708. The BPO particles 706 may possess a mean diameter ranging between about 1 to 40 μm and may be present within the non-liquid component in a concentration ranging between about 0.3 to 2 wt. % on the basis of the total weight of the non-liquid component.

In further embodiments, the BPO configuration in the non-liquid component may include a first plurality of polymer particles having BPO distributed on at least a portion of the surface of the first plurality of polymer particles and a second plurality of polymer particles having BPO substantially integrated into or intermixed in at least a portion of the second plurality of polymer particles.

Figure 19:
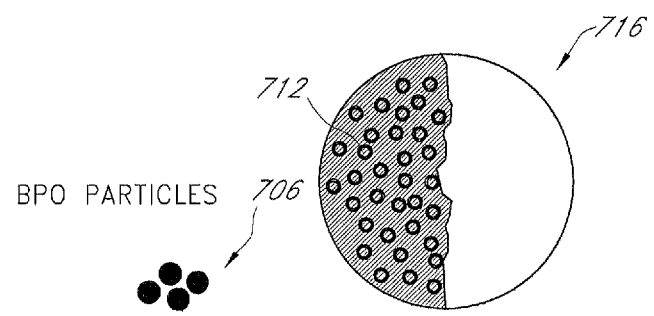
FIG. 19 show is a schematic view of polymer beads of an additional bone cement embodiment.

In another embodiment of bone cement, the BPO configuration in the non-liquid component can include polymer particles 716 with microencapsulated BPO 712 (see FIG. 19) that is substantially integrated into the polymer particles 716. These polymer particles 716 may be further combined with particles 706 of BPO. The BPO particles 706 may possess a mean diameter ranging between about 1 to 40 μm and may be present within the non-liquid component in a concentration ranging between about 0.3 to 2 wt. % on the basis of the total weight of the non-liquid component. In certain embodiments, about 10 to 90% of the total BPO content may be integrated into the polymer particles, with the remaining portion of BPO not integrated into the polymer particles. In other embodiments, about 10-90% of the total BPO content may not be integrated into the polymer particles, with the remaining portion of BPO integrated into the polymer particles.

Figure 20:
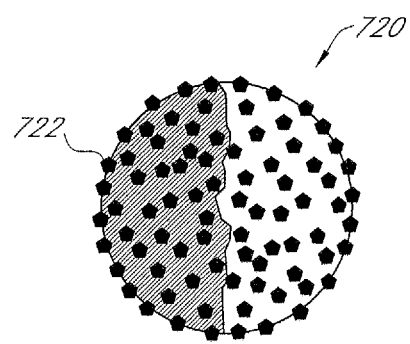
FIG. 20 is a schematic view of polymer beads of another bone cement embodiment.

In other embodiments, the BPO configuration in the non-liquid component may include particles of BPO integrated into polymer particles and particles of BPO that are not integrated into polymer particles (e.g., BPO particles 706). For example, in certain embodiments, about 10 to 90% of the total BPO content may be integrated into the polymer particles, with the remaining portion of BPO not integrated into the polymer particles. In other embodiments, about 10-90% of the total BPO content may not be integrated into the polymer particles, with the remaining portion of BPO integrated into the polymer particles. In another embodiment, the BPO configuration in the non-liquid component can include a polymer powder or particles 720 with BPO particles 722 milled into the powder particles, which can cause such BPO particles 722 to substantially adhere to a surface of the polymer power particles (see FIG. 20). Similarly, radiopacifiers can be milled into the surfaces of the polymer powder (see FIG. 20). In certain embodiments, the density of BPO particles 722 and/or radiopacifiers upon the surface of the polymer particles 720 may range between about 0.01-0.2 g/cm$^3$.

In another embodiment of bone cement, the liquid monomer component can include microencapsulated monomer volumes within a sacrificial capsule (not shown).

In further embodiments, the above disclosed bone cement compositions may be provided in such a manner that the BPO configuration controls the initiation, or the rate, of chemical reaction caused by mixing the liquid monomer component and the non-liquid component. Thus, in an embodiment of the present disclosure, controlled BPO exposure may provide a lengthened setting interval in which the mixture has a flowability property that prevents unwanted extravasation.

In an embodiment, the BPO may be provided in a configuration such that the bone cement composition exhibits a viscosity of at least about 500 Pa·s within about 30 to 90 seconds after the liquid and non-liquid components are substantially mixed with one another (e.g., post-mixing). In certain embodiments, of the method composition may achieve a viscosity of at least about 500 Pa·s, at least about 1000 Pa·s, at least about 1500 Pa·s and at least about 2000 Pa·s within about 30 seconds post-mixing. In other embodiments of the method, the composition may achieve a viscosity of at least about 500 Pa·s, at least about 1000 Pa·s, at least about 1500 Pa·s, at least about 2000 Pa·s and at least about 2500 Pa·s within about 60 seconds post-mixing. In further embodiments of the method, the composition may achieve a viscosity of at least about 500 Pa·s, at least about 1000 Pa·s, at least about 1500 Pa·s, at least about 2000 Pa·s and at least about 3000 Pa·s within about 90 seconds post-mixing.

In further embodiments, the BPO configurations within bone cement compositions discussed herein may enable the BPO that is exposed to the liquid component of the bone cement composition to be approximately constant over a selected time interval. In certain embodiments, this time interval may range between about 2 to 10 minutes. In further embodiments, the viscosity of the bone cement composition during this time interval may be greater than about 1000 Pa·s, greater than about 1500 Pa·s, greater than about 2000 Pa·s, greater than about 2500 Pa·s, greater than about 3000 Pa·s, greater than about 3500 Pa·s, and greater than about 4000 Pa·s.

In another embodiment, the BPO configuration within bone cement compositions discussed herein may control the amount of BPO that is exposed to the liquid component of the bone cement composition such that the composition exhibits a viscosity of less than about 4000 Pa·s after about 20 minutes post-mixing, after about 18 minutes post-mixing, after about 16 minutes post-mixing, after about 14 minutes post-mixing, and after about 12 minutes post-mixing. In another embodiment, the composition may achieve a viscosity of less than about 3000 Pa·s after about 20 minutes post-mixing, after about 18 minutes post-mixing, after about 16 minutes post-mixing, after about 14 minutes post-mixing, and after about 12 minutes post-mixing. In another embodiment, the composition may achieve a viscosity of less than about 2000 Pa·s after about 20 minutes post-mixing, after about 18 minutes post-mixing, after about 16 minutes post-mixing, after about 14 minutes post-mixing, and after about 12 minutes post-mixing.

In an embodiment, bone cements having such properties may include a monomer component and polymer component such as those described above. In other embodiments, the bone cements may include a monomer component and a polymer component, where the polymer component includes a first volume of beads having a first average wt. % of benzoyl peroxide (BPO), on the basis of the total weight of the first volume of beads, and a second volume of beads having a second average wt. % of BPO, on the basis of the total weight of the second volume of beads. In this bone cement embodiment, the first volume of beads may have an average cross section of less than about 100 microns, less than about 80 microns, less than about 60 microns, or less than about 40 microns. The second volume of beads may have an average cross section of greater than about 40 microns, greater than about 60 microns, greater than about 80 microns, and greater than about 100 microns. In a bone cement embodiment, the first volume may have less than about 0.5 wt. % of BPO and the second volume may have greater than about 0.5 wt. % of BPO. In another bone cement embodiment, the combined first and second volumes may also include less than about 5.0 wt. % of BPO or less than about 2.5 wt. % of BPO on the basis of the total weight of the polymer component. In a further bone cement embodiment, the combined first and second volumes have greater than about 0.5 wt. % of BPO or greater than about 1.0 wt. % of BPO. In an additional embodiment, at least a portion of the first volume is without BPO or at least a portion of the second volume is without BPO.

In another embodiment of the present disclosure, the bone cement includes a monomer component and polymer component, where the polymer component includes beads carrying from about 0.2% and 0.6% of BPO, on the basis of the total weight of the beads. In certain embodiments, at least about 80% of the BPO is carried on a first portion of beads having a mean cross section of greater than about 100 microns, and less than about 20% of the BPO is carried on a second volume of beads having a mean cross section of less than about 100 microns.

In another embodiment of the present disclosure, the bone cement includes a monomer component and polymer component, where the polymer component includes beads carrying from about 0.2% and 0.6% of BPO, on the basis of the total weight of the beads. In certain embodiments, about 100% of the BPO is carried on a first portion of the beads having a mean cross section of greater than about 100 microns, and approximately no BPO is carried on a second portion beads volume having a mean cross section less than 100 microns.

In another embodiment of the present disclosure, the bone cement includes a monomer component and polymer component, where the polymer component includes beads of at least one polymeric material. The polymer component may include from about 0.2% and 3.0% BPO on the basis of the total weight of the beads. In further embodiments, a first portion of the beads may carry BPO in a surface coating and a second portion of the beads may carry BPO integrated into the at least one polymeric material.

In another embodiment of the present disclosure, the bone cement may include a monomer component and polymer component, where the polymer component includes beads of at least one polymeric material and from about 0.2% and 3.0% BPO on the basis of the total weight of the beads. In certain embodiments, the BPO may be provided in at least two of the following forms: as a surface coating on beads, as BPO particles, as BPO in microcapsules, as BPO particles within beads of a polymeric material, and as BPO in microcapsules within beads of a polymeric material.

Figure 21:
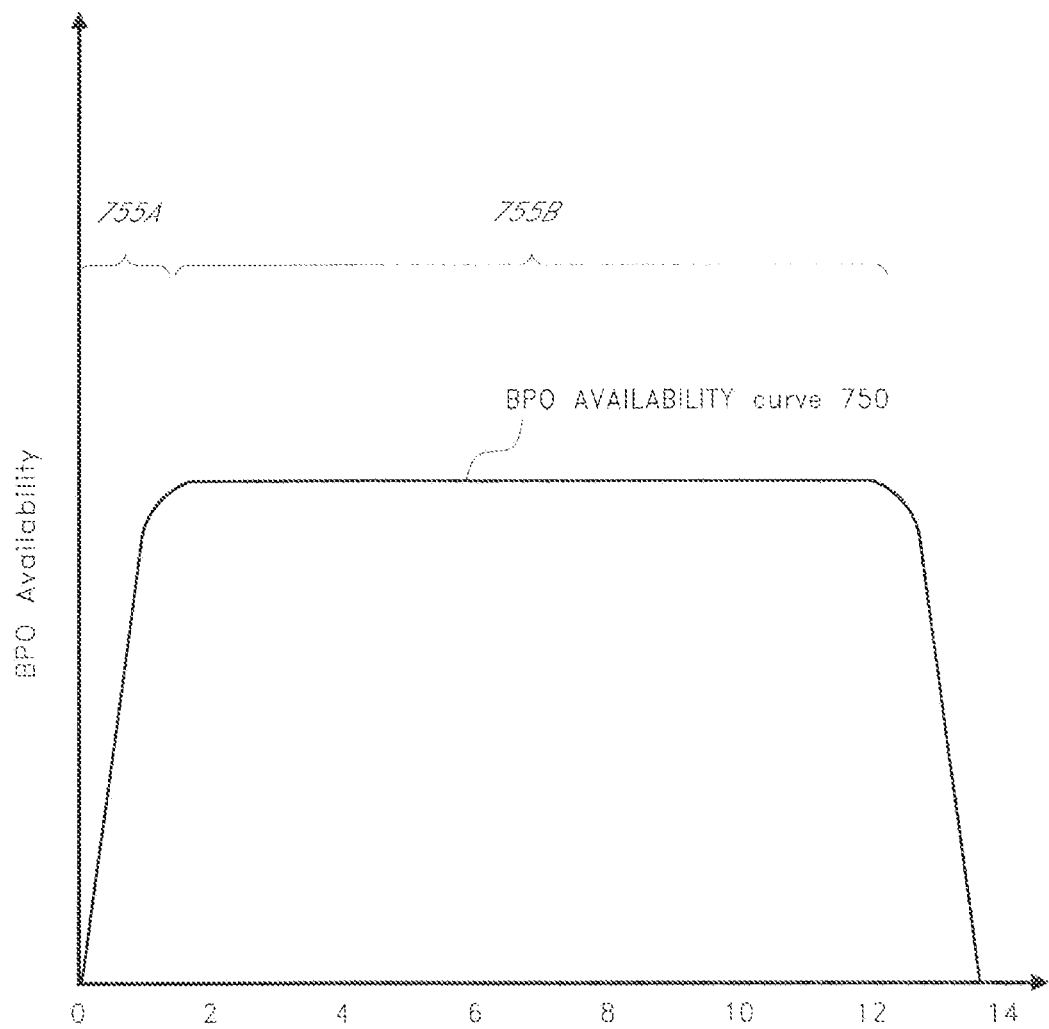
FIG. 21 is a chart indicating free indicator (BPO) available to be exposed to monomer over a post-mixing interval of a cement.

In one embodiment, depicted in FIG. 21, the concentration or volume of BPO available may be characterized in a BPO volume (or BPO surface area) versus time plot. For example, in one embodiment of the bone cement composition, the slope of the BPO availability curve 750 over time may be positive in region 755A, and thereafter the slope may be approximately zero or substantially flat (region 755B) over at least 4 minutes, 6 minutes or 8 minutes. In certain embodiments, the BPO availability within the positive region 755A may initially be zero and then reach between about 0.004 g/ml/min to 0.04 g/ml/min. Thereafter, the BPO availability may be substantially constant in the above range. In certain embodiments, the total time over which the BPO availability vs. time plot exhibits a slope that is approximately zero in a post-mixing interval can be at least 2 minutes, 4 minutes, 6 minutes, 8 minutes and 10 minutes. In another embodiment, BPO availability curve can be controlled in slope over the post-mixing period to flatten, increase in slope or decrease in slope in either direction by controlling the amount of BPO exposed to the monomer.

The BPO availability curve in FIG. 21 can be achieved, in certain embodiments, by integrating BPO into polymer particles as depicted in FIG. 16. Upon mixing liquid monomer with the particles 700 and 705, the monomer would rapidly dissolve the small particles 700 which would rapidly increase BPO availability resulting in the slope within region 755A, and after the small particles 700 were dissolved, then that larger particles 705 would dissolve slowly exposing a substantially constant amount of BPO to be wetted by the monomer in region 755B of the curve.

In another embodiment of a method of the present disclosure, a method of making a bone cement composition is provided. The method includes providing a liquid monomer component and polymer component, the polymer component having polymer particles contained therein. The method further includes distributing BPO within the polymer particles so as to provide a selected BPO availability (e.g., controlled exposure) to the liquid monomer component over at least first and second time intervals. In certain embodiments, the BPO may be selectively exposed to the liquid monomer over the at least first and second time intervals. In certain embodiments, the BPO availability per second over the first time interval is substantially greater than the BPO availability per second over the second time interval. In an embodiment, the first time interval may be at least about 1 minute, at least about 2 minutes, and at least about 3 minutes. The first time interval can be less than about 5 minutes. In other embodiments, the second time interval may be at least about 5 minutes, at least about 10 minutes, at least about 15 minutes, at least about 20 minutes, at least about 25 minutes, at least about 30 minutes, at least about 35 minutes, and at least about 40 minutes.

Figure 22:
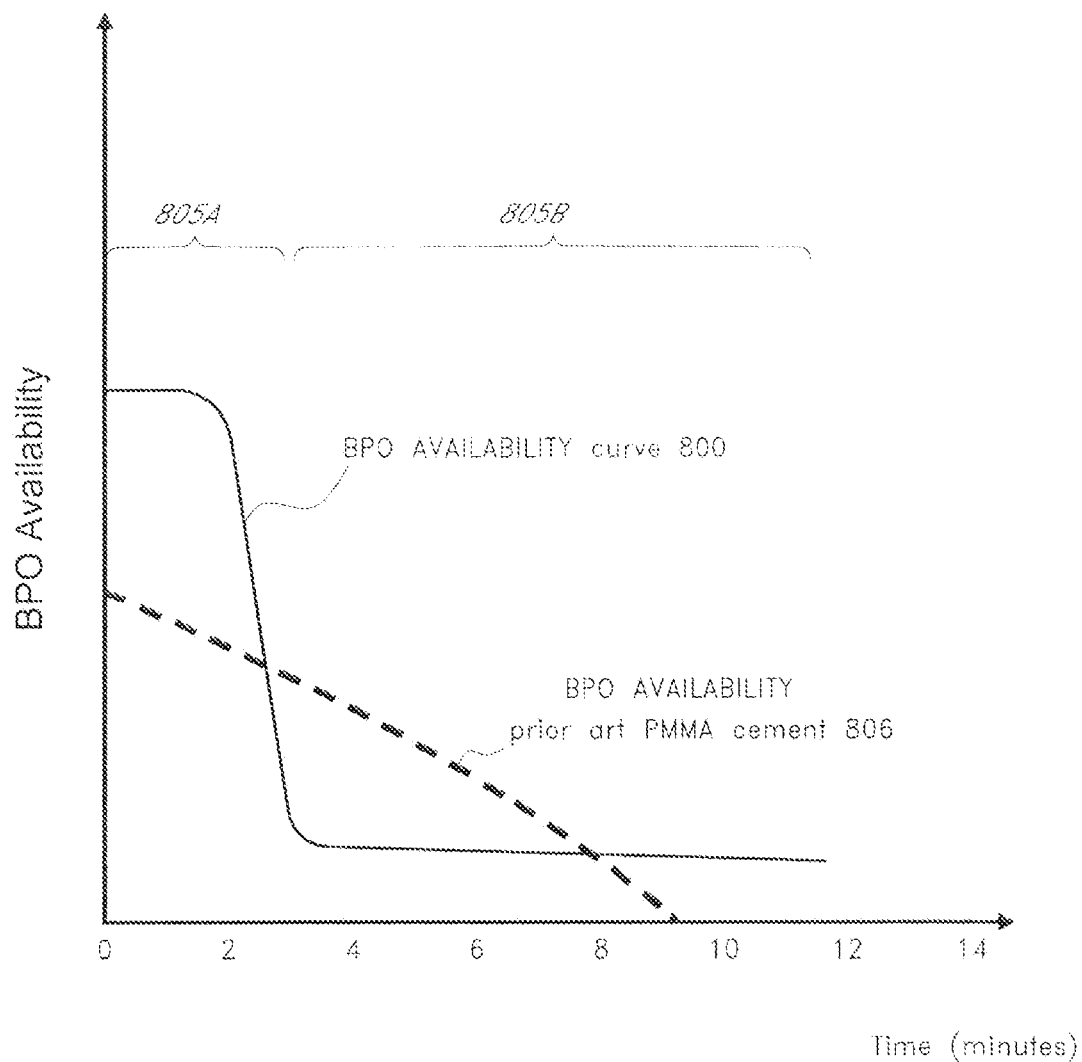
FIG. 22 is another chart indicating free initiator (BPO) available to be exposed to monomer over a post-mixing interval of a cement.

FIG. 22 illustrates another embodiment of volume or concentration of exposed BPO as a function of time. FIG. 22 illustrates curve 800 indicating BPO availability over time, indicating the amount of BPO that may be available for exposure to the monomer. The first interval 805A may fall within a range of between about 0.004 g/ml/min to 0.04 g/ml/min. FIG. 22 illustrates the second interval 805B in which the BPO availability is less than the first interval until the BPO availability is diminished as the bone cement reaches a setting point. As can be seen in FIG. 22, the composition exhibits a discontinuity in the BPO availability curve, which provides the cement with an extended working time. A bone cement and BPO availability characterized by FIG. 22 can be provided by a cement formulation described above, or with the use of BPO particles 706 as in FIGS. 17-19, or BPO surface coatings as in FIGS. 18 and 20. The method can further include mixing the liquid monomer component and the polymer component and injecting the mixture into bone. In FIG. 22, the BPO availability curve 806 of a conventional PMMA bone cement in shown.

The method can further include mixing the liquid monomer component and the polymer component and injecting the mixture into bone. In one embodiment, the BPO availability can be high for about one to five minutes post-mixing in order to accelerate an increase in viscosity, and then the BPO availability can be lower for about the next 5 to 40 minutes as the cement is further polymerizing.

Figure 23:
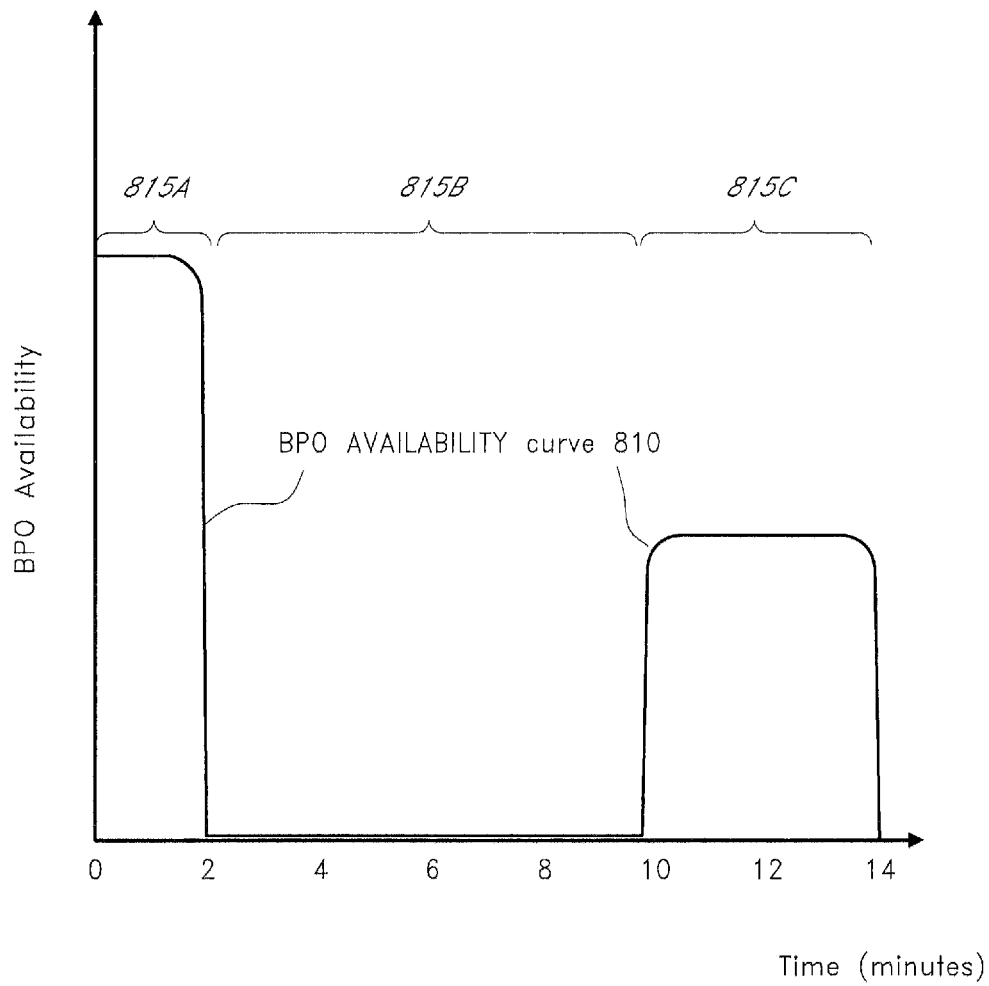
FIG. 23 is a chart indicating initiator (BPO) availability over a post-mixing interval of another cement.

In another embodiment, referring to FIG. 23, bone cement precursors can be characterized by a BPO availability curve 810 that provides high availability in a first interval 815A, as in FIG. 22, for up to about five minutes to create a rubberized cement condition suited for non-extravasating injection into bone. Thereafter, BPO availability can be reduced to about zero for a second interval 815B of about 1 to 20 minutes thus maintaining the cement substantially in the rubberized condition for injection without substantial extravasation. Thereafter, BPO availability can be increased to a high level for a third interval 815C of from 30 seconds to 5 minutes to cause rapid setting of the cement.

Figure 24:
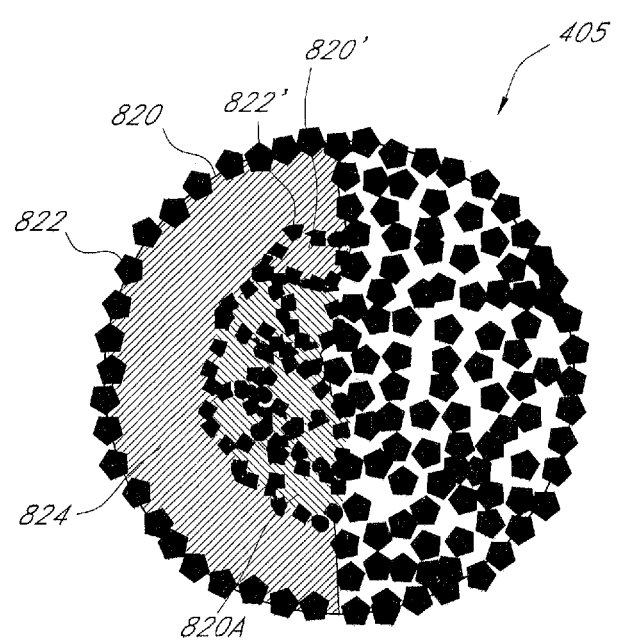
FIG. 24 is a schematic view of polymer beads of another bone cement embodiment.

Such a BPO availability curve and resulting cement may be provided by using a non-liquid component consisting of particles 405 as depicted in FIG. 24. In FIG. 24, the BPO particles 822 are milled on the surface of particles of PMMA material 820, similar to that of FIG. 20. A surface layer of PMMA material 824 interior of the BPO particles 822 is without any BPO. Further interior of the PMMA layer 820A, fragmented particles of BPO coated PMMA particles 820A, with BPO indicated at 822' and PMMA material indicated at 820B.

Figure 25:
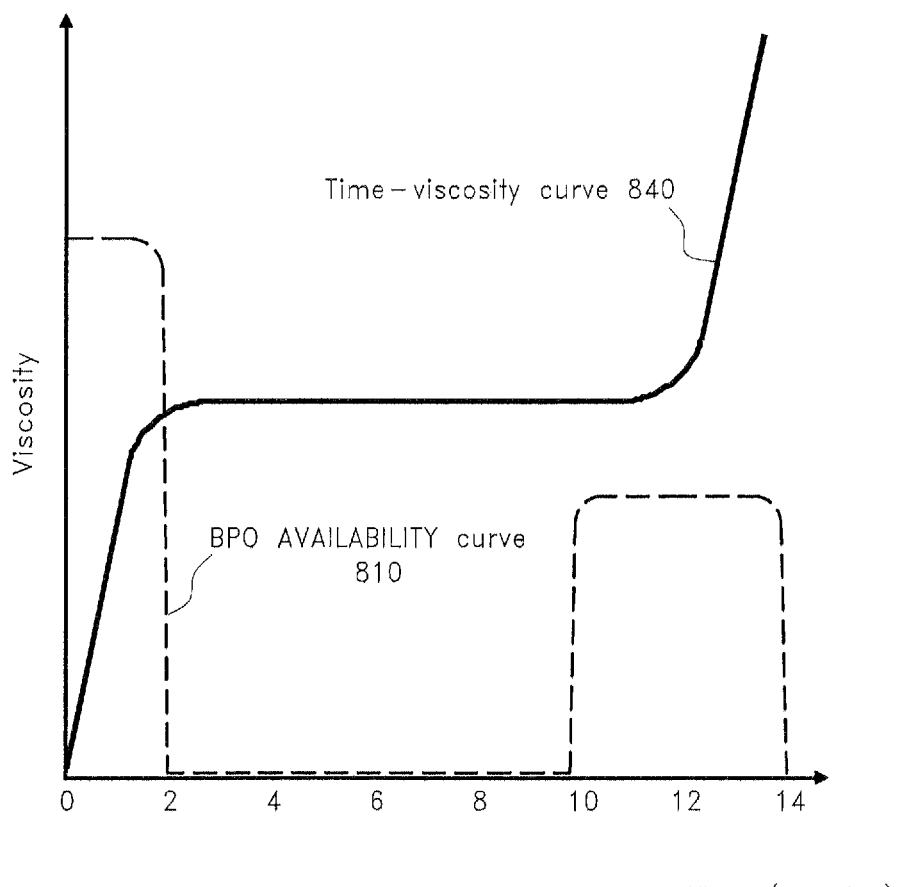
FIG. 25 is a chart indicating a time viscosity curve of cement shown in FIG. 23 over a post-mixing interval.

It can be understood that upon exposure to the liquid component in mixing, the monomer is initially exposed to the milled BPO surface 822, wetting the surface and thus providing the high BPO availability indicated by the first interval 815A of FIG. 23. Thereafter, the BPO availability would drop to zero as indicated in second interval 815B of FIG. 23. During this interval, the monomer would slowly dissolve the layer of PMMA material 824. At a selected subsequent point in time, depending on the selected thickness of the PMMA layer 824, the monomer would reach the BPO layer 822' and thus BPO availability would increase as shown in third interval 815C of FIG. 23. The packed together particles 820 can separate and all BPO surface areas of these particles may then be exposed to the monomer. A bone cement composition that results from mixing liquid and non-liquid components as described above would then provide a cement composition having a time-viscosity curve 840 as shown in FIG. 25, which is superimposed over the BPO availability curve of FIG. 23.

In certain embodiments of this method, the selected BPO availability is provided by at least two different particles having differing BPO configurations therein. In one embodiment, the selected BPO exposure may be provided by a controlling BPO exposure to the monomer component on at least a portion of the surface area of the particles. In another embodiment, the selected BPO exposure may be provided, at least in part, by particles comprising a mixture of a polymeric material and BPO. In another embodiment, the selected BPO exposure may be provided, at least in part, by particles having a surface coating of BPO. In another embodiment, the selected BPO exposure may be provided, at least in part by, microencapsulated BPO. In another embodiment, the selected BPO exposure may be provided by particles having layers of polymeric materials and BPO.

In another embodiment of a method of the present disclosure, the mixable bone cement may exhibit a selected interval in which the release or exposure of BPO or other initiator is controlled. In this manner, a selected concentration or volume of free BPO within the composition may be achieved over a selected time interval. In one embodiment, free BPO includes the volume of BPO, or other initiator, that is available or exposed to the liquid monomer post-mixing.

In one specific formulation of a PMMA bone cement, the solid or powder component of the bone cement may include: PMMA, BPO, and $ZrO_2$. In one embodiment, polymethylmethacrylate polymer (PMMA) is present within the bone cement in a concentration ranging between about 45%-55 wt. % on the basis of the total weight of the powder component. In other embodiments, the concentration of PMMA is about 49.6 wt. %. In other embodiments, the Benzoyl Peroxide (BPO) is present in a concentration ranging between about 0.30-0.80% on the basis of the total weight of the powder component In other embodiments, the concentration of BPO is about 0.40 wt. %. In additional embodiments, the concentration of Zirconium Dioxide or Barium Sulfate may range between about 45%-55% on the basis of the total weight of the powder component. In another embodiment, the concentration of Zirconium Dioxide or Barium Sulfate is less than or equal to about 50.0 wt. %.

In this cement formulation, the liquid component of the bone cement includes Methylmethacrylate (MMA), N, N-dimethyl-p-toluidine (DMPT), and Hydroquinone (HQ). In one embodiment, the concentration of Methylmethacrylate (MMA) may range between about 98.0-99.9 wt. % on the basis of the total weight of the liquid component. In other embodiments, the concentration of MMA may be about 99.5%. In other embodiments, the concentration of DMPT may range between about 0.15-0.95 wt. % on the basis of the total weight of the liquid component. In other embodiments, the concentration of DMPT may be about 0.50%. In other embodiments, the concentration of HQ may range between about 30-150 ppm on the basis of the total amount of the liquid component. In other embodiments, the concentration of HQ may be about 75 ppm.

In embodiments of this cement formulation, the powder PMMA component as described above may include a blend of a plurality of PMMA powders distinguished by one or more of PMMA molecular weights, particle sizes, and/or concentrations of BPO contained within the powder.

For example, in one embodiment of the bone cement composition, three (3) PMMA powders, Powders 1, 2 and 3, may be provided. The ratio of amounts of each of powders 1, 2, and 3 may range between about 40 to 50% for powder 1, 30 to 40% for powder 2, and the remainder comprising powder 3. In one embodiment, powders 1, 2, and 3 are mixed in a ratio of: Powder 1=44.28%; Powder 2=36.86% and Powder 3=18.86%.

Powder 1 may include a target particle size having a range of about 100-120 μm, for example, about 110 microns. The molecular weight of PMMA of powder 1 may range between about 150,000 to 350,000, for example, about 350,000. Powder 1 may further include about 0.9-1.1 wt. % BPO on the basis of the total weight of the powder component. In certain embodiments, powder 1 may include about 1.0 wt. % BPO.

Powder 2 may include a target particle size having a range of about 70-90 µm, for example, about 80 microns. The molecular weight of PMMA of powder 2 may range between about 300,000 to 500,000, for example, about 400,000. Powder 2 may further include about 1.1 to 1.3 wt. % BPO on the basis of the total weight of the powder component. In certain embodiments, powder 2 may include about 1.2 wt. % BPO.

Powder 3 may include a target particle size having a range of about 25 to 45 µm, for example, about 35 microns. The molecular weight of PMMA of powder 3 may range between about 250,000 to 450,000, for example, about 250,000. Powder 3 may further include about 0.0-1.1 wt. % BPO on the basis of the total weight of the powder component. In certain embodiments, powder 3 may include approximately no BPO.

In some conventional vertebroplasty and kyphoplasty procedures, bone cement is injected into a fractured vertebral body to act as an internal cast to stabilize the fractured bone. Stabilization of the fracture can eliminate micromotion, which typically can eliminate pain associated with the fracture. A typical bone cement includes a self-curing polymer such as PMMA that is produced by mixing a first liquid monomer component and a second non-liquid polymer component. Many commercially available bone cements use methyl methacrylate as a liquid monomer component and methylmethacrylate as a principal powder component. After mixing the first and second components, the mixture sets or self-cures upon polymerization and crosslinking of the components.

In RF kyphoplasty, which can use a system with a heating element to apply energy to the bone cement as described above, the bone cement can be formulated for application of heat from an RF source to cause rapid, controlled polymerization and greater viscosity during injection to inhibit unwanted extravasation. In such an RF kyphoplasty procedure, the applied energy is complementary to the self-curing chemical reaction that occurs upon mixing a monomer and polymer.

Figure 26:
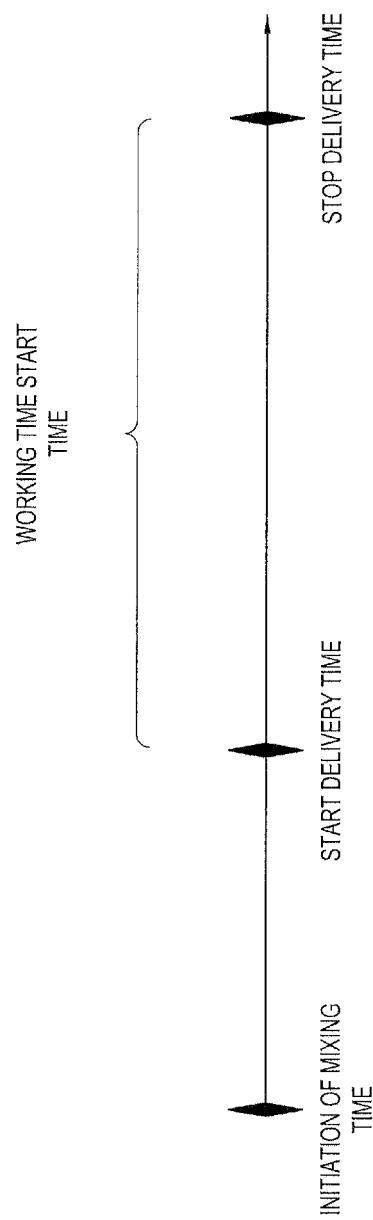
FIG. 26 is a diagram showing certain time intervals for an bone cement in use.

In an operating environment, bone cement for conventional vertebroplasty/kyphoplasty procedures and/or RF kyphoplasty is typically mixed at a back table in an operating room immediately before its injection into a patient. There are at least two important, and related, operating parameters relating to the preparation and use of a self-curing bone cement, which are indicated in FIG. 26. A first operating parameter is the "start time" or "start delivery time" which is a predetermined number of minutes post-mixing generally characterized by a certain degree of polymerization of the cement mixture which allows for flowability as well as a desired viscosity. The "post-mixing" time refers to minutes post or after the "initiation of mixing time" (see FIG. 26) of the bone cement components. A second important operating parameter is total "working time" of the cement, which is the time interval between the start delivery time and a stop delivery time—the point in time that the cement is too viscous to be injected. Whether the bone cement is too viscous can depend on many factors, such as the delivery pressures and the desired delivery viscosity. In some embodiments, it can be desirable to deliver bone cement at about 3,000-6,000 Pa*s, or at about 5,000-9,000 Pa*s. In some embodiments, the bone cement can be too viscous at about or greater than: 10,000, 12,000, or 15,000 Pa*s. Another operating parameter is the cement viscosity itself—which preferably is a predictable minimum level that can be determined by the interval of minutes post-mixing and thus is directly related to the start-time. The viscosity parameter can be important for preventing extravasation and also for determining injection pressure requirements over the interval of the cement working time. Another time point beyond the end of the working time interval is the set time, at which time the cement is cured or substantially cured. The set time thus also can be calculated relative to the initiation of mixing time.

The polymerization and curing of bone cements can be retarded by cool temperatures in an operating environment or accelerated by warm temperatures in an operating room, thus affecting the start delivery time and cement working time. Likewise, if the cement precursors (monomer and polymer) are stored in a cooler or warmer temperature relative to the operating environment, the variance in temperatures can also affect the cement operating parameters.

Referring back to FIG. 14, as was discussed previously, this chart shows the change in viscosity over time of a bone cement when heated to different temperatures. A similar chart could be made showing the differences in viscosity over time with different starting temperatures. In general, as in FIG. 14, the higher the start temperature the faster the viscosity increase over time. In one embodiment, a controller (e.g., electronic or computer controller) such as the controller 145 can control the operation of the system 10 for delivering bone cement based at least in part on an algorithm that models the different rate of viscosity increase of a bone cement at different starting temperatures.

For example, in one embodiment, assuming a default or set desired delivery viscosity, a physician or nurse with a starting temperature of the bone cement precursors can then determine the bone cement delivery start time with the use of a chart or a computer program or controller (e.g., electronic or computer controller), such as the controller 145. In some embodiments, the user can start with both the starting temperature and the desired viscosity and determine the bone cement delivery start time.

In another aspect, a method of using a curable bone cement in a surgical procedure can be provided which can include the steps of (1) acquiring temperature data of at least one bone cement precursor prior to mixing the at least two bone cement precursors; and (2) acquiring and/or generating a signal of an operating parameter of the cement to thereby allow a controller and/or physician to alter a procedural step. More specifically, one preferred operating parameter is a temperature of a bone cement precursor.

In another aspect relating to components of FIGS. 6, 27 and 28, a kit that includes bone cement pre-cursors such as a liquid monomer component and/or a non-liquid polymer component, can further include a temperature sensor carried on the surface of a container of either or both precursors, or on a surface of the packaging or mixing assembly. The temperature of the component or components can then be taken into consideration to determine the start-time for using the mixed cement. In general, a kit for providing a self-curing bone cement can include a first container containing a first component of the bone cement, and a second container containing a second component of the bone cement, wherein at least one container has a surface carrying a sensor 274. The sensor 274 can be one of many different types of sensors including a temperature sensor.

FIG. 27 shows a temperature sensor 274 affixed to a monomer vial 271. FIG. 28 shows a temperature sensor 274 affixed to packaging 273 of a monomer vial 271. In some embodiments, the temperature sensor 274 can be a temperature strip 278. The temperature strip can be a thermostrip device available from LCR Hallcrest, also known as Liquid Crystal Resources, LLC, 1820 Pickwick Lane, Glenview, Ill. 60026. In one embodiment, the temperature strip 278 can include micro-encapsulated liquid crystal compounds that carry an ink or dye that change color based on temperature. Such liquid crystals include chemical compounds that exhibit the mechanical properties of liquids and the optical characteristics of solids, and are known as thermochromic liquid crystals (TLC's), or as cholesteric liquid crystals.

In some embodiments, one or more of the bone cement precursors can control the temperature or greatly influence the temperature of the bone cement. For example, in some embodiments, a liquid monomer can change temperature at a slower rate than a powder component. In some embodiments, the start temperature can be the temperature of a bone cement precursor or the temperature history of the bone cement precursor. In some embodiments, a temperature sensor, such as the temperature sensor 274, can be on or in the packaging and/or container of only one of the bone cement precursors, such as the precursor whose starting temperature has the greatest influence on the rate of viscosity change of the bone cement.

In some embodiments, the packaging and/or container holding a liquid monomer component can include a temperature sensor, such as a temperature strip (e.g., the temperature strip 278). Where, for example, a cold monomer component can warm slowly and the temperature of a PMMA powder can very quickly adjust to ambient room temperature, the temperature of the liquid monomer can be used to determine the rate of change of the viscosity over time of the bone cement after the bone cement components are mixed together.

In some embodiments a method can include the step of placing one or more of the bone cement precursors in the ambient atmosphere of a treatment room for a desired period of time prior to mixing. In some embodiments, said desired period of time prior to mixing can include at least about: 30, 45, and 60 minutes prior to mixing. In some embodiments, a start temperature can include the ambient room temperature, especially where one or more of the bone cement precursors are exposed to the ambient temperature of a treatment room prior to mixing.

In some embodiments, a kit carries at least one temperature sensor 274 that can include a visual display, that can further include a thermochromic ink or thermochromic liquid crystals.

In other embodiments, a kit carries at least one temperature sensor that includes a wireless transmitter (e.g., RF transmitter) component for transmitting the temperature data to another device (e.g., to a computer controller) in a wireless manner.

In other embodiments, a kit includes a wireless device 277 (e.g., RF transmitter, RF tag) for conveying information data to another device 279 (e.g., to a computer controller) in a wireless manner. The wireless device 277 can convey information on its own or in response to a signal from another device 279. The data can include data about the product, such as, whether the product is a liquid monomer or a powder component, or sensor data, such as, temperature or temperature history. The wireless transmitter 277 can be a stand alone device or can be part of the sensor 274. The other device, such as a computer controller, can provide the conveyed information, and/or additional information to other devices and/or operators.

In one embodiment, the container 271 carrying the sensor can be a vial containing a liquid monomer or a body containing a powder. The body can be a vial, ampule, tube, syringe, bag or sac. Alternatively, the sensor can be affixed to packaging 273, which can include at least one of a shipping carton, box, bag, tube, sterile pouch, sterile sac and blister pack. The sensor 274 can be on an interior or exterior surface.

In some embodiments, a system for providing a bone cement for injection into a patient, can include a first package containing a liquid monomer and a second package containing a polymer powder; a data transmitter (e.g., a radio frequency tag/temperature sensor) carried by at least one package to provide output data; and a data receiver for receiving the output data and providing a signal to a controller and/or system operator. The output data can include an ID parameter selected from the group of monomer or polymer type, volume of monomer or polymer, and manufacturing lot of the monomer of polymer. Further, the output data can include a temperature of the monomer or polymer, or a temperature log or history of the monomer or polymer. The system can be configured to provide signals that are at least one of electronic data or an audible, visual or tactile signal.

In some embodiments, a system can provide a signal that indicates a post-mixing start time for injecting the cement. In some embodiments, the signal can indicate a stop time for injecting the cement, cement viscosity, or cement temperature.

A method for providing operational information concerning a bone cement can include (1) providing one or more bone cement precursors of bone cement in a kit with a temperature sensor affixed thereto; (2) mixing the bone cement precursors to provide a bone cement; and (3) determining the bone cement injection start time based on temperature of one or more of the bone cement precursors. The method can have a determining step that is derived from a chart, or the determining step can be provided by an algorithm and computer controller.

Another method for providing operational information concerning a bone cement can include (1) providing one or more bone cement precursors of bone cement in a kit with a radio frequency tag affixed thereto; (2) transmitting an interrogation signal to the radio frequency tag from a controller; (3) receiving a response signal from the radio frequency tag indicating data concerning one or more bone cement precursors; and (4) determining an operational step based on the data. The data can include temperature and/or temperature history. The operational step can be the cement delivery start time or the cement delivery stop time.

Another method can determine a working condition of a curable bone cement, wherein the steps of the method can include (1) determining the pre-mix temperature of at least one of first and second bone cement precursors; (2) determining the ambient temperature; (3) mixing the first and second bone cement precursors; and (4) utilizing an algorithm relating to pre-mix and ambient temperatures to thereby determine a cement injection start time. The method can further include actuating a controller and energy source to apply energy through an emitter to thereby apply heat to the bone cement post-mixing. The method can further include actuating the controller to modulate applied energy based on the pre-mix and ambient temperatures and/or the calculated injection start time. The method can further include actuating the controller to modulate hydraulic pressure based on the pre-mix and ambient temperatures and/or the calculated injection start time.

In the above methods, the determining steps can be accomplished at least by one temperature sensor affixed to containers and/or packaging of the first and second bone cement precursors.

Another aspect can provide a method of determining a working condition of a curable bone cement which can include (1) determining the pre-mix temperature history of at least one of the first and second bone cement precursors; (2) determining the ambient temperature; (3) mixing the first and second bone cement precursors; and (4) utilizing an algorithm relating to pre-mix and ambient temperatures to thereby determine a cement injection start time.

A method of using a curable bone cement in a surgical procedure can include (1) acquiring temperature data of at least one bone cement precursor prior to mixing at least two bone cement precursors; and (2) generating a signal of an operating parameter of the cement to thereby allow a controller and/or physician to alter a procedural step.

Specific characteristics and features of the systems and methods are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. Consequently, the scope of the present teachings should not be limited to the foregoing discussion, but should be defined by the appended claims.

Of course, the foregoing description is that of certain features, aspects and advantages of the present invention, to which various changes and modifications can be made without departing from the spirit and scope of the present invention. Moreover, the bone treatment systems and methods need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A bone cement kit package, comprising:
   a first container containing a liquid component comprising a monomer;
   a second container containing a non-liquid component comprising at least two polymer bead populations having different average sizes and different weight percentages of a radical initiator,
   wherein the liquid component and the non-liquid component are configured to, upon mixing, form a mixture that cures at least in part by self-heating by undergoing an exothermic reaction; and
   a temperature sensor affixed to an outer surface of a packaging material of the bone cement kit package and used to indicate a pre-mix temperature of at least one of the non-liquid component and the liquid component inside the bone cement kit package prior to mixing the non-liquid component and the liquid component together.

2. The bone cement kit package of claim 1, wherein one of the polymer bead populations having a smaller average size than another one of the polymer bead populations has a higher weight percentage of the initiator than the another one of the polymer bead populations.

3. The bone cement kit package of claim 1, wherein the liquid component comprises an activator at a concentration less than about 1% based on an overall weight of the liquid component.

4. The bone cement kit package of claim 3, wherein the initiator comprises benzoyl peroxide (BPO) and the activator comprises N,N-dimethyl-p-toluidine (DMPT).

5. The bone cement kit package of claim 1, wherein the liquid component and the non-liquid component are configured to, upon mixing, self-heat the mixture to a peak temperature not exceeding 75 degrees.

6. The bone cement kit package of claim 1, wherein the pre-mix temperature has been predetermined to have an associated post-mixing setting time.

7. The bone cement kit package of claim 6, wherein the associated post-mixing setting time is greater than 25 minutes.

8. A bone cement kit package, comprising:
   a first container containing a liquid component comprising a monomer;
   a second container containing a non-liquid component comprising at least two polymer bead populations having different average sizes and different weight percentages of a radical initiator,
   wherein the liquid component and the non-liquid component are configured to, upon mixing, form a mixture that cures at least in part by self-heating by undergoing an exothermic reaction; and
   a temperature sensor affixed to an outer surface of one of the first and second containers having a component whose pre-mix temperature changes at a slower rate compared to the other one of the first and second containers having another component, wherein the temperature sensor is used to indicate a pre-mix temperature of at least one of the non-liquid component and the liquid component inside the bone cement kit package prior to mixing the non-liquid component and the liquid component together.

9. The bone cement kit package of claim 8, wherein one of the polymer bead populations having a smaller average size than another one of the polymer bead populations has a higher weight percentage of the initiator than the another one of the polymer bead populations.

10. The bone cement kit package of claim 8, wherein the liquid component comprises an activator at a concentration less than about 1% based on an overall weight of the liquid component.

11. The bone cement kit package of claim 10, wherein the initiator comprises benzoyl peroxide (BPO) and the activator comprises N,N-dimethyl-p-toluidine (DMPT).

12. The bone cement kit package of claim 8, wherein the liquid component and the non-liquid component are configured to, upon mixing, self-heat the mixture to a peak temperature not exceeding 75 degrees.

13. The bone cement kit package of claim 8, wherein the pre-mix temperature has been predetermined to have an associated post-mixing setting time.

14. The bone cement kit package of claim 13, wherein the associated post-mixing setting time is greater than 25 minutes.

15. The bone cement kit package of claim 8, wherein the sensor is affixed to the first container containing the liquid component.

* * * * *